(12) United States Patent
Tabirian et al.

(10) Patent No.: US 11,366,254 B2
(45) Date of Patent: Jun. 21, 2022

(54) HIGH-EFFICIENCY WIDE-ANGLE BEAM STEERING SYSTEM

(71) Applicant: Beam Engineering for Advanced Measurements Co., Orlando, FL (US)

(72) Inventors: Nelson Tabirian, Winter Park, FL (US);
David E. Roberts, Apopka, FL (US);
Sarik Nersisyan, Oviedo, FL (US);
Olena Uskova, Winter Park, FL (US);
Anna Tabirian, Winter Park, FL (US)

(73) Assignee: BEAM ENGINEERING FOR ADVANCED MEASUREMENTS CO., Orlando, FL (US)

( * ) Notice: Subject to any disclaimer, the term of this patent is extended or adjusted under 35 U.S.C. 154(b) by 224 days.

(21) Appl. No.: 16/746,366

(22) Filed: Jan. 17, 2020

(65) Prior Publication Data

US 2020/0150324 A1 May 14, 2020

Related U.S. Application Data

(63) Continuation-in-part of application No. 16/220,995, filed on Dec. 14, 2018, now Pat. No. 10,557,977, (Continued)

(51) Int. Cl.
*G02B 6/00* (2006.01)
*G02B 6/12* (2006.01)
(Continued)

(52) U.S. Cl.
CPC .......... *G02B 5/1833* (2013.01); *A61F 2/1618* (2013.01); *A61F 2/1654* (2013.01);
(Continued)

(58) Field of Classification Search
CPC ...... G02B 5/1833; G02B 3/0081; G02B 3/10; G02B 5/001; G02B 5/1828; G02B 5/3083;
(Continued)

(56) References Cited

U.S. PATENT DOCUMENTS 2,435,616 A 2/1948 Vittum
3,721,486 A 3/1973 Bramley
(Continued)

FOREIGN PATENT DOCUMENTS

EP 1970734 9/2008
EP 2088456 12/2009
(Continued)

OTHER PUBLICATIONS

Tabiryan, et al., The Promise of Diffractive Waveplates, OPN Optics and Photonics News, Mar. 2010, 6 pages.
(Continued)

*Primary Examiner* — Kaveh C Kianni
*Assistant Examiner* — Hung Q Lam
(74) *Attorney, Agent, or Firm* — Brian S. Steinberger; Hilary F. Steinberger; Law Offices of Brian S. Steinberger, P.A.

(57) ABSTRACT

Optical beam steering and focusing systems, devices, and methods that utilize diffractive waveplates are improved to produce high efficiency at large beam deflection angles, particularly around normal incidence, by diffractive waveplate architectures comprising a special combination of liquid crystal polymer diffractive waveplate both layers with internal twisted structure and at a layer with uniform structure.

8 Claims, 13 Drawing Sheets

Related U.S. Application Data which is a continuation of application No. 14/688,425, filed on Apr. 16, 2015, now Pat. No. 10,191,191, said application No. 16/220,995 is a continuation-in-part of application No. 14/688,197, filed on Apr. 16, 2015, now Pat. No. 10,274,650, which is a continuation-in-part of application No. 13/916,627, filed on Jun. 13, 2013, now abandoned, which is a continuation of application No. 12/697,083, filed on Jan. 29, 2010, now abandoned.

(60) Provisional application No. 61/980,062, filed on Apr. 16, 2014.

(51) Int. Cl.

| | | |
|---|---|---|
| *G02B 6/32* | (2006.01) | |
| *G02B 6/028* | (2006.01) | |
| *G02B 6/10* | (2006.01) | |
| *G02B 5/18* | (2006.01) | |
| *G02B 27/42* | (2006.01) | |
| *G02B 3/00* | (2006.01) | |
| *G02B 6/35* | (2006.01) | |
| *G02B 6/024* | (2006.01) | |
| *G02B 5/00* | (2006.01) | |
| *G02B 5/30* | (2006.01) | |
| *A61F 2/16* | (2006.01) | |
| *G02C 7/08* | (2006.01) | |
| *G02B 3/10* | (2006.01) | |
| *G02C 7/12* | (2006.01) | |
| *G02C 7/06* | (2006.01) | |
| *G02C 7/02* | (2006.01) | |
| *G02C 7/10* | (2006.01) | |

(52) U.S. Cl.
CPC .......... *G02B 3/0081* (2013.01); *G02B 3/10* (2013.01); *G02B 5/001* (2013.01); *G02B 5/1828* (2013.01); *G02B 5/3083* (2013.01); *G02B 6/024* (2013.01); *G02B 6/3534* (2013.01); *G02B 6/3592* (2013.01); *G02B 27/4205* (2013.01); *G02B 27/4211* (2013.01); *G02B 27/4216* (2013.01); *G02B 27/4261* (2013.01); *G02C 7/022* (2013.01); *G02C 7/061* (2013.01); *G02C 7/086* (2013.01); *G02C 7/12* (2013.01); *G02C 7/10* (2013.01); *G02C 2202/16* (2013.01); *G02C 2202/20* (2013.01)

(58) Field of Classification Search
CPC .... G02B 6/024; G02B 6/3534; G02B 6/3592; G02B 27/4205; G02B 27/4211; G02B 27/4216; G02B 27/4261; G02B 5/1814; G02B 5/1871; G02B 26/0808; G02B 3/0087; A61F 2/1618; A61F 2/1654; G02C 7/022; G02C 7/061; G02C 7/086; G02C 7/12; G02C 7/10; G02C 2202/16; G02C 2202/20; G02C 7/083
USPC .............. 385/11, 14, 33, 124, 129
See application file for complete search history.

(56) References Cited

U.S. PATENT DOCUMENTS

| | | |
|---|---|---|
| 3,897,136 A | 7/1975 | Bryngdahl |
| 4,160,598 A | 7/1979 | Firester et al. |
| 4,301,023 A | 11/1981 | Schuberth |
| 4,698,816 A | 10/1987 | Chun |
| 4,956,141 A | 9/1990 | Allen |
| 4,983,332 A | 1/1991 | Hahn |
| 5,032,009 A | 7/1991 | Gibbons |
| 5,042,950 A | 8/1991 | Salmon, Jr. |
| 5,047,847 A | 9/1991 | Toda |
| 5,100,231 A | 3/1992 | Sasnett et al. |
| 5,142,411 A | 8/1992 | Fiala |
| 5,150,234 A | 9/1992 | Takahashi |
| 5,218,610 A | 6/1993 | Dixon |
| 5,321,539 A | 6/1994 | Hirabayashi |
| 5,325,218 A | 6/1994 | Willett |
| 5,446,596 A | 8/1995 | Mostrorocco |
| 5,619,325 A | 4/1997 | Yoshida |
| 5,621,525 A | 4/1997 | Vogeler et al. |
| 5,712,721 A | 1/1998 | Large |
| 5,895,422 A | 4/1999 | Hauber |
| 5,903,330 A | 5/1999 | Funschilling |
| 5,907,435 A | 5/1999 | Ang |
| 5,989,758 A | 11/1999 | Komatsu |
| 6,091,471 A | 7/2000 | Kim |
| 6,107,617 A | 8/2000 | Love et al. |
| 6,139,147 A | 10/2000 | Zhang |
| 6,170,952 B1 | 1/2001 | La Haye et al. |
| 6,191,880 B1 | 2/2001 | Schuster |
| 6,219,185 B1 | 4/2001 | Hyde |
| 6,320,663 B1 | 11/2001 | Ershov |
| 6,373,549 B1 | 4/2002 | Tombling et al. |
| 6,452,145 B1 | 9/2002 | Graves et al. |
| 6,551,531 B1 | 4/2003 | Ford |
| 6,678,042 B2 | 1/2004 | Tabirian et al. |
| 6,728,049 B1 | 4/2004 | Tabirian et al. |
| 6,792,028 B2 | 9/2004 | Cook |
| 6,911,637 B1 | 6/2005 | Vorontsov et al. |
| 7,048,619 B2 | 5/2006 | Park |
| 7,094,304 B2 | 8/2006 | Nystrom |
| 7,095,772 B1 | 8/2006 | Delfyett et al. |
| 7,196,758 B2 | 3/2007 | Crawford |
| 7,319,566 B2 | 1/2008 | Prince |
| 7,324,286 B1 * | 1/2008 | Glebov ................ G02F 1/135 359/30 |
| 7,450,213 B2 | 11/2008 | Kim et al. |
| 7,482,188 B2 | 1/2009 | Moon |
| 7,764,426 B2 | 7/2010 | Lipson |
| 8,045,130 B2 | 10/2011 | Son |
| 8,077,388 B2 | 12/2011 | Gerton |
| 8,264,623 B2 | 9/2012 | Marrucci |
| 8,520,170 B2 | 8/2013 | Escuti |
| 8,582,094 B1 | 11/2013 | Shortt |
| 8,643,822 B2 | 2/2014 | Tan et al. |
| 8,937,701 B2 | 1/2015 | Rossini |
| 8,982,313 B2 | 3/2015 | Escuti et al. |
| 9,535,258 B1 | 1/2017 | Whiteaker |
| 9,541,772 B2 | 1/2017 | De Sio et al. |
| 9,557,456 B2 | 1/2017 | Tabirian et al. |
| 9,592,116 B2 | 3/2017 | De Sio et al. |
| 9,617,205 B2 | 4/2017 | Tabirian et al. |
| 9,658,512 B2 | 5/2017 | Tabirian et al. |
| 9,715,048 B2 | 7/2017 | Tabirian et al. |
| 9,753,193 B2 | 9/2017 | Tabirian et al. |
| 9,976,911 B1 | 5/2018 | Tabirian et al. |
| 9,983,479 B2 | 5/2018 | Tabirian et al. |
| 10,031,424 B2 | 7/2018 | Tabirian et al. |
| 10,036,886 B2 | 7/2018 | Tabirian et al. |
| 10,075,625 B2 | 9/2018 | Tabirian et al. |
| 10,107,945 B2 | 10/2018 | Tabirian et al. |
| 10,114,239 B2 | 10/2018 | Tabirian et al. |
| 10,120,112 B2 | 11/2018 | Tabirian et al. |
| 10,185,182 B2 | 1/2019 | Tabirian |
| 10,191,191 B2 | 1/2019 | Tabirian et al. |
| 10,191,296 B1 | 1/2019 | Tabirian et al. |
| 10,197,715 B1 | 2/2019 | Tabirian et al. |
| 10,274,650 B2 | 4/2019 | Tabirian et al. |
| 10,330,947 B2 | 6/2019 | Tabirian et al. |
| 10,423,045 B2 | 9/2019 | Tabirian et al. |
| 10,436,957 B2 | 10/2019 | Tabirian et al. |
| 2001/0002895 A1 | 6/2001 | Kawano |
| 2001/0018612 A1 | 8/2001 | Carson et al. |
| 2001/0030720 A1 | 10/2001 | Ichihashi |
| 2002/0027624 A1 | 3/2002 | Seiberle |
| 2002/0097361 A1 | 7/2002 | Ham |
| 2002/0167639 A1 | 11/2002 | Coates |

(56) References Cited

U.S. PATENT DOCUMENTS

| | | |
|---|---|---|
| 2003/0021526 A1 | 1/2003 | Bouevitch |
| 2003/0072896 A1 | 4/2003 | Kwok |
| 2003/0137620 A1 | 7/2003 | Wang |
| 2003/0152712 A1 | 8/2003 | Motomura |
| 2003/0206288 A1 | 11/2003 | Tabirian et al. |
| 2003/0214700 A1 | 11/2003 | Sidorin |
| 2003/0218801 A1 | 11/2003 | Korniski et al. |
| 2004/0051846 A1 | 3/2004 | Blum et al. |
| 2004/0081392 A1 | 4/2004 | Li |
| 2004/0105059 A1 | 6/2004 | Ohyama |
| 2004/0165126 A1 | 8/2004 | Ooi et al. |
| 2005/0030457 A1 | 2/2005 | Kuan et al. |
| 2005/0110942 A1 | 5/2005 | Ide |
| 2005/0219696 A1 | 10/2005 | Albert et al. |
| 2005/0271325 A1 | 12/2005 | Anderson et al. |
| 2005/0276537 A1 | 12/2005 | Frisken |
| 2005/0280717 A1 | 12/2005 | Chen |
| 2006/0008649 A1 | 1/2006 | Shinichiro |
| 2006/0055883 A1 | 3/2006 | Morris et al. |
| 2006/0109532 A1 | 5/2006 | Savas |
| 2006/0221449 A1 | 10/2006 | Glebov et al. |
| 2006/0222783 A1 | 10/2006 | Hayashi |
| 2007/0032866 A1 | 2/2007 | Portney |
| 2007/0040469 A1 | 2/2007 | Yacoubian |
| 2007/0115551 A1 | 5/2007 | Spilman |
| 2007/0122573 A1 | 5/2007 | Yasuike |
| 2007/0132930 A1 | 6/2007 | Ryu et al. |
| 2007/0247586 A1 | 10/2007 | Tabirian |
| 2007/0258677 A1 | 11/2007 | Chigrinov |
| 2008/0226844 A1 | 9/2008 | Shemo |
| 2008/0278675 A1 | 11/2008 | Escuti |
| 2009/0002588 A1 | 1/2009 | Lee et al. |
| 2009/0052838 A1 | 2/2009 | McDowall |
| 2009/0073331 A1 | 3/2009 | Shi |
| 2009/0122402 A1 | 5/2009 | Shemo |
| 2009/0141216 A1 | 6/2009 | Marrucci |
| 2009/0201572 A1 | 8/2009 | Yonak |
| 2009/0256977 A1 | 10/2009 | Haddock |
| 2009/0257106 A1 | 10/2009 | Tan |
| 2009/0264707 A1 | 10/2009 | Hendricks |
| 2010/0003605 A1 | 1/2010 | Gil |
| 2010/0066929 A1 | 3/2010 | Shemo |
| 2010/0245954 A1 | 9/2010 | Ahling |
| 2011/0069377 A1 | 3/2011 | Wu et al. |
| 2011/0075073 A1 | 3/2011 | Oiwa |
| 2011/0085117 A1 | 4/2011 | Moon et al. |
| 2011/0097557 A1 | 4/2011 | May |
| 2011/0109874 A1 | 5/2011 | Piers et al. |
| 2011/0135850 A1 | 6/2011 | Saha et al. |
| 2011/0188120 A1 | 8/2011 | Tabirian et al. |
| 2011/0234944 A1 | 9/2011 | Powers |
| 2011/0262844 A1 | 10/2011 | Tabirian |
| 2012/0075168 A1 | 3/2012 | Osterhout et al. |
| 2012/0140167 A1 | 6/2012 | Blum |
| 2012/0162433 A1 | 6/2012 | Fuentes Gonzalez |
| 2012/0188467 A1 | 7/2012 | Escuti |
| 2013/0057814 A1 | 3/2013 | Prushinskiy et al. |
| 2013/0202246 A1 | 8/2013 | Meade |
| 2014/0055740 A1 | 2/2014 | Spaulding |
| 2014/0211145 A1 | 7/2014 | Tabirian |
| 2014/0252666 A1 | 9/2014 | Tabirian |
| 2015/0049487 A1 | 2/2015 | Connor |
| 2015/0077700 A1* | 3/2015 | De Sio ............... A61F 2/1654 351/159.03 |
| 2015/0081016 A1 | 3/2015 | De Sio et al. |
| 2015/0276997 A1 | 10/2015 | Tabirian et al. |
| 2016/0011564 A1 | 1/2016 | Tanabe et al. |
| 2016/0023993 A1 | 1/2016 | Tabirian |
| 2016/0047955 A1 | 2/2016 | Tabirian et al. |
| 2016/0047956 A1 | 2/2016 | Tabirian et al. |
| 2016/0209560 A1 | 7/2016 | Tabirian et al. |
| 2016/0231592 A9 | 8/2016 | Beaton et al. |
| 2016/0270656 A1 | 9/2016 | Samec et al. |
| 2016/0363484 A1 | 12/2016 | Barak et al. |
| 2016/0363783 A1 | 12/2016 | Blum |
| 2017/0010397 A1 | 1/2017 | Tabirian et al. |
| 2019/0113777 A1 | 4/2019 | Tabirian et al. |

FOREIGN PATENT DOCUMENTS

| | | |
|---|---|---|
| GB | 2209751 | 5/1989 |
| JP | 2001142033 | 5/2001 |
| JP | 2004226752 | 8/2004 |
| WO | 2007122573 | 11/2007 |
| WO | 2008130555 | 10/2008 |
| WO | 2008130559 | 10/2008 |

OTHER PUBLICATIONS

Tabiryan, et al., Fabricating Vector Vortex Waveplates for Coronagraphy; Aerospace Conference, 2012, EEE; publicly available Apr. 19, 2012, 12 pages.

Tabirian, et al., PCT Application No. PCT/US15/261 86 filed Apr. 16, 2015, Notification of Transmittal of the International Search Report and the Written Opinion of the International Searching Authority dated Jul. 14, 2015, 17 pages.

Nersisyan, et al., Study of azo dye surface command photoalignment material for photonics applications, Applied Optics, vol. 49, No. 10, Apr. 1, 2010, 8 pages.

Nersisyan, et al., Characterization of optically imprinted polarization gratings, Applied Optics, vol. 48, No. 21, Jul. 20, 2009, 6 pages.

Nersisyan, et al., Fabrication of Liquid Crystal Polymer Axial Waveplates for UV-IR Wavelengths, Optics Express, vol. 17, No. 14, Jul. 2009, 9 pages.

Nersisyan, et al., Optical Axis Gratings in Liquid Crystals and Their Use for Polarization Insensitive Optical Switching, Journal of Nonlinear Optical Physics & Materials, vol. 18, No. 1, 2009, 47 pages.

Nersisyan, et al., Polarization insensitive imaging through polarization gratings, Optics Express, vol. 17, No. 3, Feb. 2, 2009, 14 pages.

Sarkissian, et al., Longitudinally modulated nematic bandgap structure, Optical Society of America, vol. 23, No. 8, Aug. 2008, 6 pages.

Sarkissian, et al., Polarization—universal bandgap in periodically twisted nematics, Optics Letters, vol. 31, No. 11, Jun. 1, 2006, abstract, 4 pages.

Sarkissian, et al., Periodically Aligned Liquid Crystal: Potential Application for Projection Displays, Mol. Cryst. Liq. Cryst., vol. 451, 2006, 19 pages.

Sarkissian, et al., Potential application of Periodically Aligned Liquid Crystal cell for projection displays, JThE12, 2005, 3 pages.

Sarkissian, et al., Polarization—Controlled Switching Between Diffraction Orders in Transverse-Periodically Aligned Nematic Liquid Crystals, Optics Letters, Aug. 2006, abstract, 4 pages.

Schadt, et al., Photo—Induced Alignment and Patterning of Hybrid Liquid Crystalline Polymer Films on Single Substrates, Jpn. J. Appl. Phys., vol. 34, Part 2, No. 6B, Jun. 15, 1995, 4 pages.

Schadt , et al., Photo-Generation of Linearly Polymerized Liquid Crystal Aligning Layers Comprising Novel, Integrated Optically Patterned Retarders and Color Filters, Jpn. J. Appl. Phys., vol. 34, Part 1, No. 6A, Jun. 1995, 10 pages.

Schadt, et al., Optical patterning of multi-domain liquid-crystal displays with wide viewing angles, Nature, vol. 381, May 16, 1996, 4 pages.

Escuti, et al., A Polarization—Idependent Liquid Crystal Saptial-Light-Modulator, Liquid Crystals X, Proc. of SPIE, vol. 6332, 2006, 9 pages.

Escuti, et al., Polarization—Independent LC Microdisplays Using Liquid Crystal Polarization Gratings: A Viable Solution (?), Dept of Electrical & Computer Engineering @ ILCC, Jul. 1, 2008, 30 pages.

Escuti, et al., Simplified Spectropolarimetry Using Reactive Mesogen Polarization Gratings, Imaging Spectrometrv XI, Proc. of SPIE, vol. 6302, 2006, 11 pages.

Gibbons, et al., Surface-mediated alignment of nematic liquid crystals with polarized laser light, Nature, vol. 351, May 2, 1991, 1 page.

(56) References Cited

OTHER PUBLICATIONS

Gibbons, et al., Optically Controlled Alignment of Liquid Crystals: Devices and Applications, Molecular Crystals and Liquid Crystals, vol. 251, 1994, 19 pages.

Gibbons, et al., Optically generated liquid crystal gratings, Appl. Phys. Lett., 65, Nov. 14, 1994, 3 pages.

University of Central Florida, School of Optics CREOL PPCE, Optics in the Southeast, Technical Conference and Tabletop Exhibit, Nov. 12-13, 2003, 9 pages.

Ichimura, et al., Surface assisted photoalignment contiol of lyotropic liquid crystals, Part 1, Characterization and photoalignment of aqueous solutions of a water soluble dyes as lyotropic liquid crystals, J. Materials. Chem., vol. 12, 2002, abstract, 2 pages.

Ichimura, et al., Reversible Change in Alignment Mode of Nematic Liquid Crystals Regulated Photochemically by "Command Surfaces" Modified with an Azobenzene Monolayer, American Chemical Society, Langmuir, vol. 4, No. 5, 1988, 3 pages.

Zel'Dovich, et al., Devices for displaying visual information, Disclosure, School of Optics/CREOL, University of Central Florida, Jul. 2000, 10 pages.

Provenzano, et al., Highly efficient liquid crystal based diffraction grating induced by polarization holograms at the aligning surfaces, Applied Physics Letter 89, 2006, 4 pages.

Titus, et al., Efficient polarization-independent, re ective liquid crystal phase grating, Applied Physics Letter 71, Oct. 20, 1197, 3 pages.

Chen, et al. An Electrooptically Controlled Liquid-Crystal Diffraction Grating, Applied Physics Letter 67, Oct. 30, 1995, 4 pages.

Kim et al., Unusual Characteristics of Diffraction Gratings in a Liquid Crystal Cell, Advanced Materials, vol. 14, No. 13-14, Jul. 4, 2002, 7 pages.

Pan, et al., Surface Topography and Alignment Effects in UV-Modified Polyimide Films with Micron Size Patterns, Chinese Journal of Physics, vol. 41, No. 2, Apr. 2003, 8 pages.

Fuh, et al., Dynamic studies of holographic gratings in dye-doped liquid-crystal films, Optics Letter, vol. 26, No. 22, Nov. 15, 2001, 3 pages.

Yu, et al., Polarization Grating of Photoaligned Liquid Crystals with Oppositely Twisted Domain Structures, Molecular Crystals Liquid Crystals, vol. 433, 2005, 7 pages.

Crawford, et al., Liquid-crystal diffraction gratings using polarization holography alignment techniques, Journal of Applied Physics 98, 2005, 10 pages.

Seiberle, et al., 38.1 Invited Paper: Photo-Aligned Anisotropic Optical Thin Films, SID 03 Digest, 2003, 4 pages.

Wen, et al., Nematic liquid-crystal polarization gratings by modification of surface alignment, Applied Optics, vol. 41, No. 7, Mar. 1, 2002, 5 pages.

Anagnostis, et al., Replication produces holographic optics in volume, Laser Focus World, vol. 36, Issue 3, Mar. 1, 2000, 6 pages.

Gale, Replicated Diffractive Optics and Micro-Optics, Optics and Photonics News, Aug. 2003, 6 pages.

McEldowney, et al., Creating vortex retarders using photoaligned LC polymers, Optics Letter, vol. 33, No. 2, Jan. 15, 2008, 3 pages.

Stalder, et al., Lineraly polarized light with axial symmetry generated by liquid-crystal polarization converters, Optics Letters vol. 21, No. 1996, 3 pages.

Kakichashvili, et al., Method for phase polarization recording of holograms, Sov. J. Quantum. Electron, vol. 4, No. 6, Dec. 1974, 5 pages.

Todorov, et al., High-Sensitivity Material with Reversible Photo-Induced Anisotropy, Optics Communications, vol. 47, No. 2, Aug. 15, 1983, 4 pages.

Attia, et al., Anisoptropic Gratings Recorded From Two Circularly Polarized Coherent Waves, Optics Communications, vol. 47, No. 2, Aug. 15, 1983, 6 pages.

Cipparrone, et al., Permanent polarization gratings in photosensitive langmuir blodget films, Applied Physics Letter, vol. 77, No. 14, Oct. 2, 2000, 4 pages.

Nikolova, et al., Diffraction Efficiency and Selectivity of Polarization Holographic Recording, Optica Acta: International Journal of Optics, vol. 31, No. 5, 1984, 11 pages.

Lee et al., "Generation of pretilt angles of liquid crystals on cinnamte-based photoalignment . . .", Opt., Expr., vol. 17 (26) (Dec. 2009), abstract, 4 pages.

Yaroshchuk et al. "Azodyes as photoalignment agents for polymerizable liquid crystals", IDW'06 Digest vol. 1-3, 2006, 4 pages.

Chigrinov et al. "Anchoring properties of photoaligned azo-dye materials" Phys. Rev., E vol. 68, (Dec. 2003), 5 pages.

Pagliusi et al. Surface-induced photorefractivity in twistable nematics: toward the all-optical control of gain, Opt. Expr. vol. 16, Oct. 2008, 9 pages.

M. Honma, T. Nose, Polarization—independent liquid crystal grating fabricated by microrubbing process, Jpn. J. Appl. Phys., Part 1, vol. 42, 2003, 3 pages.

Anderson, G., et al., Broadband Antihole Photon Sieve Telescope, Applied Optics, vol. 16, No. 18., Jun. 2007, 3 pages.

Early, J. et al., Twenty Meter Space Telescope Based on Diffractive Fresnel Lens, SPIE, U.S. Department of Energy, Lawrence Livermore National Laboratory, Jun. 2003, 11 pages.

Martinez-Cuenca, et al., Reconfigurable Shack-Hartmann Sensor Without Moving Elements, Optical Society of America, vol. 35, No. 9, May 2010, 3 pages.

Serak, S., et al., High-efficiency 1.5 mm Thick Optical Axis Grating and its Use for Laser Beam Combining, Optical Society of America, vol. 32, no., Jan. 2007, 4 pages.

Ono et al., Effects of phase shift between two photoalignment substances on diffration properties in liquid crystalline grating cells, Appl. Opt. vol. 48, Jan. 2009, 7 pgs.

Naydenova et al., "Diffraction form polarization holographic gratings with surface relief in side chain azobenzene polyesters" J. Opt. Soc. Am. B, vol. 15, (1998), 14 pages.

Oh et al., Achromatic polarization gratings as highly efficent thin-film polarizing beamsplitters for broadband light Proc. SPIE vol. 6682, (2007), 4 pages.

Nersisyan, S., et al., Polarization insensitive imaging through polarization gratins, Optics Express, vol. 17, No. 3, Feb. 2, 2009, 14 pages.

Oise, Optics in the Southeast, Technical Conference and Tabletop Exhibit, Optical Society of America, Orlando, FL., Nov. 12-13, 2003, 9 pages.

Dierking, Polymer Network-Stabilized Liquid Crystals, Advanced Materials, vol. 12, No. 3, 2000, 15 pages.

Tabiryan, et al., Broadband waveplate lenses, Optics Express 7091, vol. 24, No. 7, Mar. 24, 2016, 12 pages.

Tabiryan, et al. Thin waveplate lenses of switchable focal length—new generation in optics, Optics Express 25783, vol. 23, No. 20, Sep. 19, 2015, 12 pages.

Tabiryan, et al. Superlens in the skies: liquid-crystal-polymer technology for telescopes, Newsroom, 2016, 2 pages.

Nersisyan, et al., The principles of laser beam control with polarization gratings introduced as diffractive waveplates, Proc. of SPIE, vol. 7775, 2010, 10 pages.

Heller, A Giant Leap for Space Telescopes, Foldable Optics, S&TR, Mar. 2003, 7 pages.

Beam Engineering for Advanced Measurements Co., PCT Application No. PCT/US2015026186, The Extended European Search Report, filed on Mar. 8, 2017, 13 pages.

Blinov, et al., Electrooptic Effects in Liquid Crystal MAterials, Springer-Verlag New York, 1994, 17 pages.

Crawford, et al., Liquid Crystals in Complex Geometries; Formed by Polymer and Porous Networks, Taylor and Francis, 1996, 4 pages.

Honma, et al., Liquid-Crystal Fresnel Zone Plate Fabricated by Microorubbing, Japanese Journal of Applied Physics, vol. 44, No. 1A, 2005, 4 pages.

Tabirian, N., et al., U.S. Appl. No. 61/757,259, filed Jan. 28, 2013, 29 pages.

Beam Engineering for Advaced Measurements Co., et al., PCT Application No. PCT/US2016/038666 filed Jun. 22, 2016, Notification of Transmittal of the International Search Report and the

(56) References Cited

OTHER PUBLICATIONS

Written Opinion of the International Searching Authority, or the Declaration dated Oct. 10, 2016, 16 pages.
Marrucci, et al., Pancharatnam—Berry phase optical elements for wave front shaping in the visible domain, Appl. Phys. Lett. 88, 2006, 3 pages.
Sobolewska et al., "On the inscription of period and half period surface relief gratings in azobenzene-functionalized polymers", J. Phys. Chem., vol. 112 (15) Jan. 3, 2008, 10 pages.
Barrett et al., Model of laser driven mass transport in thin films of dye-functionalized polymers, J. Chem. Phys., vol. 109 (4), Jul. 22, 1998, 13 pages.
Vernon, J., et al, Recording Polarization Gratings with a Standing Spiral Wave, Applied Physics Letters, Oct. 2013, vol. 103, 4 pages.
Gerchberg, et al, practical algorithm for the determination of the phase from image and diffraction plane pictures, 1972, Optik, vol. 35, Issue 2, pp. 237-246, 10 pages.
Serak, et al. Diffractive Waveplate Arrays [Invited], Journal of the Optical Society of America B, May 2017, pp. B56-B63, vol. 34, No. 5, 8 pages.
Emoto, Optical and Physical Applications of Photocontrollable Materials: Azobenzene—Containing and Liquid Crystalline Polymers, Polymers, Jan. 2012, 150-186, vol. 4, 38 pgs.
Pepper, M. et al, Nonlinear Optical Phase Conjugation, IEEE, Sep. 1991, pp. 21-34, 14 pages.
De Sio, L., et al., "Digital Polarization Holography Advancing Geometrical Phase Optics," 2016, Optics Express, vol. 24, Issue 16, pp. 18297-18306, 10 pages.
Borek, G. and D. Brown, "High-performance diffractive optics for beam shaping," 1999, Proceeding of SPIE, vol. 3633, pp. 51-60, 10 pages.
Roberts, D. et al, "Polarization-Independent Diffractive Waveplate Optics," Mar. 2018, IEEE Aerospace Conference, 11 pages.

\* cited by examiner

HIGH-EFFICIENCY WIDE-ANGLE BEAM STEERING SYSTEM

CROSS REFERENCE TO RELATED APPLICATIONS

This application is a Continuation-In-Part of U.S. patent application Ser. No. 16/220,995 filed Dec. 14, 2018, now allowed, which is a Continuation of U.S. patent application Ser. No. 14/688,425 filed Apr. 16, 2015, now U.S. Pat. No. 10,191,191, which claims the benefit of priority to U.S. Provisional Application Ser. No. 61/980,062 filed Apr. 16, 2014, and this application is a Continuation-In-Part of U.S. patent application Ser. No. 16/220,995 filed Dec. 14, 2018, now allowed, which is a Continuation-In-Part of U.S. patent application Ser. No. 14/688,197 filed Apr. 16, 2015, now U.S. Pat. No. 10,274,650, which claims the benefit of priority to U.S. Provisional Patent Application Ser. No. 61/980,062 filed Apr. 16, 2014, and U.S. patent application Ser. No. 14/688,197 filed Apr. 16, 2015, now U.S. Pat. No. 10,274,650, is a Continuation-In-Part of U.S. patent application Ser. No. 13/916,627 filed Jun. 13, 2013, Abandoned, which is a Continuation of U.S. patent application Ser. No. 12/697,083 filed Jan. 29, 2010, Abandoned. The entire disclosure of the applications listed in this paragraph are incorporated herein by specific reference thereto.

FIELD OF THE INVENTION

This invention relates generally to the field of optics, and in particular to diffractive optical lenses, structures, waveplates, devices, systems and methods, which steer optical beams and optical fields of view over wide angles with high efficiency, or focus optical beams incident over a wide angular range.

BACKGROUND OF THE INVENTION

Diffractive optical structures are used in many ways in optics. Common uses are as dispersive elements in spectrometers and in lens systems. In this context, an optical structure that is "dispersive" is one for which the effect on optical radiation reflecting from, or transmitting through, the optical structure is highly dependent on wavelength. For example, over a wide range of conditions, the angle through which optical radiation is diffracted by the simplest diffractive optical structures is approximately proportional to the wavelength. This is in contrast with the angle through which optical radiation is refracted by common optical refractive materials such as glass or transparent plastic. For such refractive materials, the angle through which optical radiation is refracted is nearly independent of the wavelength.

Methods have recently been developed for fabrication of a type of transmissive diffractive optical structure variously described in the literature by the terms diffractive waveplate, polarization grating, Pancharatnam phase device, Pancharatnam-Berry optical element, or geometric phase grating. Diffractive optical structures described by these terms have the property that diffraction of optical radiation results from the spatial modulation of the optical anisotropy axis in an anisotropic optical material. For our purposes, we will refer to such diffractive optical structures as diffractive waveplates.

The simplest type of diffractive waveplate includes a film of anisotropic material whose optical anisotropy axis varies only along one Cartesian coordinate, rotating at a constant spatial speed in the plane of the film, and does not vary along the other Cartesian coordinate in the plane of the film, nor along the Cartesian coordinate perpendicular to the plane of the film. We will refer here to such a diffractive waveplate as a regular cycloidal diffractive waveplate (CDW) as the end of the vector describing the alignment of the optical anisotropy axis is drawing a cycloid upon rotation. This type of diffractive waveplate has the property that any monochromatic plane wave incident on it will be deflected by a fixed angle.

Another type of diffractive waveplate includes a film of anisotropic material whose optical anisotropy axis varies only radially from a central point in the plane of the film. For the special case in which the optical anisotropy axis varies only radially from a central point in the plane of the film, and does not vary in the direction perpendicular to the film comprising the diffractive waveplate lens, and in addition the orientation angle of the optical anisotropy axis is a quadratic function of the distance from the central point, the diffractive waveplate will be referred to in this disclosure as a regular circular diffractive waveplate lens. Other types of diffractive waveplate lens include the type in which the orientation angle of the optical anisotropy axis is a quadratic function of distance from a central line. This type of diffractive waveplate lens will be referred to in this disclosure as a cylindrical diffractive waveplate lens.

It is well known in the art that the diffraction efficiency of such a regular CDW or regular diffractive waveplate lens approaches 100% for sufficiently small angles of incidence and angles of diffraction at a particular optical wavelength $\lambda$ when the thickness of the film satisfies the so-called half-wave retardation condition at the particular wavelength. This condition is $L\Delta n=\lambda/2$, where L is the thickness of the film; and $\Delta n$ is the birefringence of the anisotropic material. The birefringence is defined as $\Delta n=n_e-n_o$, where $n_e$ is the extraordinary index of refraction, and $n_o$ is the ordinary index of refraction of the birefringent material comprising the CDW.

In contrast to some other types of diffractive elements, the diffraction efficiency of a regular CDW is relatively high over a wide range of angles of incidence, angles of diffraction, and wavelengths. Therefore, this simplest type of CDW is adequate for many uses, provided the required angles of incidence and diffraction angles are not too large, and provided the wavelength range over which the diffraction efficiency must be high is not too wide.

CDWs are used in beam steering systems in order to point laser beams and the fields of view of camera systems. For small beam steering angles and small changes in the angular position of the center of the field of view, regular CDWs have sufficiently high diffraction efficiency. However, for large steering angles and large changes in the angular position of the center of the steered field of view, the diffraction efficiency of regular CDWs can become unacceptably low for some applications. This is in part because the angles of incidence on CDWs included in such beam steering systems and field of view steering systems are large, decreasing the diffraction efficiency of CDWs.

One way to obtain high diffraction efficiency from CDWs in beam steering systems and field of view steering systems is to assure that the angle of incidence on each CDW contained in such systems is small. However, some beam steering systems and field of view steering systems are required to deflect optical radiation through large angles, so it is impossible to keep the angles of incidence small in such systems.

There are many advantages to using CDWs in beam steering systems and field of view steering systems, including size, weight, and cost advantages over more conventional steering systems involving, for example, gimballed mirrors. However, these advantages are not available using prior art because the need for large diffraction angles conflicts with the need for high diffraction efficiency.

Thus, there is a need for beam steering systems and field of view steering systems employing diffractive waveplates that maintain high diffraction efficiency over a wide range of angles of incidence.

The diffraction efficiency of a diffractive waveplate lens depends on many factors, including the angle of incidence and the f-number of the lens. The f-number is defined in this disclosure as the ratio of the focal length of the lens at an operating wavelength to the diameter of the lens, in the case in which the lens is a circular diffractive waveplate lens. The f-number is defined in this disclosure as the ratio of the focal length of the lens at an operating wavelength to the width of the lens, in the case in which the lens is a cylindrical diffractive waveplate lens.

For small f-numbers, the angle through which optical radiation is diffracted by a diffractive waveplate lens becomes large near the edges of the lens. Using prior art, this results in reduced diffraction efficiency for optical radiation diffracted from near the edges of the lens. Using prior art, the diffraction efficiency of a diffractive waveplate lens also is reduced when the angle of incidence of optical radiation on the lens becomes large.

There are many advantages to using diffractive waveplate lenses in systems, including size, weight, and cost advantages over more conventional optical systems involving, for example, curved mirrors and curved refractive elements. However, these advantages are not available using prior art because the need for large diffraction angles and large angles of incidence conflicts with the need for high diffraction efficiency.

Thus, there is a need for diffractive waveplate lenses with small f-number that maintain high diffraction efficiency over a wide range of angles of incidence.

SUMMARY OF THE INVENTION

A primary objective of this invention is to provide diffractive optical structures, waveplates, devices, systems and methods, which can steer optical beams and optical fields of view over wide angles with high efficiency.

It is another objective of the present invention to provide beam steering structures, waveplates, devices, systems, and field of view structures, waveplates, devices, steering systems and methods that employ diffractive waveplate devices in order to provide the size, weight, and cost advantages of these devices.

It is another objective of the present invention to provide diffractive waveplate lenses with small f-number that operate with high efficiency over a wide range in angles of incidence, in order to provide the size, weight, and cost advantages of these devices.

For uses in which the diffraction efficiency must be high over a wide range of wavelengths, CDWs and diffractive waveplate lenses have been developed that have high efficiency over a broader band of wavelengths that regular CDWs and regular diffractive waveplate lenses. One of the types of CDW and diffractive waveplate lens having high efficiency over a broader band of wavelengths than regular CDWs and regular diffractive waveplate lenses is the so-called twist-uniform-twist (TUT) CDW and TUT diffractive waveplate lens. For the TUT CDW, the optical anisotropy axis orientation varies along only one Cartesian coordinate in the plane of the CDW film, as is the case with regular CDWs, but unlike the case of regular CDWs, the optical anisotropy axis orientation of TUT CDWs also varies along the Cartesian coordinate perpendicular to the surfaces of the CDW film. For the TUT diffractive waveplate lens, the optical anisotropy axis orientation varies along only in one or both of the Cartesian coordinates in the plane of the film comprising the diffractive waveplate lens, as is the case with regular diffractive waveplate lenses, but unlike the case of regular diffractive waveplate lenses, the optical anisotropy axis orientation of TUT diffractive waveplate lenses also varies along the Cartesian coordinate perpendicular to the surfaces of the film comprising the diffractive waveplate lens.

One of the key innovations of the present invention is to use TUT CDWs in beam steering systems designed to steer a monochromatic beam or a narrow-band field of view over a wide range of angles. It has been proven experimentally that TUT CDWs have the property that their diffraction efficiency at a selected operating wavelength, or over a narrow band of operating wavelengths, is higher at steep angles of incidence than is the case with regular CDWs. Therefore, there are significant benefits to using TUT CDWs in beam steering systems for which the angular range of beam steering or field of view steering is large.

Another of the key innovations of the present invention is to use TUT diffractive waveplate lenses in optical systems designed to accept optical beams over a wide range of incident angles, and to diffract optical beams through steep angles. There are significant benefits to using TUT diffractive waveplate lenses in optical systems requiring small f-numbers or steep angles of incidence.

It is well known in the art that a type of CDW known as a polarization volume grating (PVG) can have a diffraction efficiency approaching approximately 100% for a normally-incident beam of a specific circular polarization, even if the diffraction angle is large. See D. Roberts, S. Kaim, N. Tabiryan, M. McConney, T. Bunning, "Polarization-Independent Diffractive Waveplate Optics," Proc. of IEEE Aerospace Conference (28 Jun. 2018), presented at the IEEE conference on Mar. 3-10, 2018, which is non-essential subject matter incorporated by reference in its entirety.

Therefore, to maximize the diffraction efficiency of a beam steering system employing CDWs, it is desirable that in beam steering and field of view steering systems employing CDWs, the first CDW encountered by a normally incident beam of known, fixed circular polarization be a PVG. It is an object of the present invention to provide beam steering systems such that the first CDW encountered by a beam of known, fixed polarization is encountered at normal incidence, and is a PVG, and that subsequent CDWs encountered along the path of an optical beam through the beam steering system be TUT CDWs.

A preferred embodiment of a beam steering system can include an optical assembly that includes at least one cycloidal diffractive waveplate, each cycloidal diffractive waveplate having three functional layers, in all of which an optical anisotropy axis is parallel to a surface of the cycloidal diffractive waveplate, in outer two layers of at least one cycloidal diffractive waveplate, the optical anisotropy axis has an orientation varying linearly with position in a direction perpendicular to the surface of the cycloidal diffractive waveplate, in an inner layer of at least one cycloidal diffractive waveplate, the optical anisotropy axis orientation having no variation with position in the direction perpendicular to the surface of the cycloidal diffractive waveplate, a twist angle of the optical anisotropy axis orientation in one of the two outer layers of at least one cycloidal diffractive waveplate being equal in magnitude and opposite in sign to the twist angle of the optical anisotropy axis orientation of the other outer layer of the cycloidal diffractive waveplate, and a controller assembly configured and arranged such that propagation direction of a beam of optical radiation traversing the optical assembly is changed by a selected angle.

The beam steering system can further include a product of thickness and birefringence of the outer two layers of at least one of cycloidal diffractive waveplate being about 30% of an intended operating wavelength of the beam steering system, and a product of the thickness and birefringence of the inner layer of at least one cycloidal diffractive waveplate being about 63% of the intended operating wavelength of the beam steering system; the absolute value of the angle through which the optical anisotropy axis twists in the two outer layers of at least one cycloidal diffractive waveplate being about 82 degrees.

The optical assembly can further include a first cycloidal diffractive waveplate and a second cycloidal diffractive waveplate, the first cycloidal diffractive waveplate receiving a normally incident optical beam having a polarization volume grating structure providing high diffraction efficiency at a selected operating wavelength of the beam steering system, and the optical assembly can include components so that the rotational positions of the first and the second cycloidal diffractive waveplates are independently controlled by the controller assembly.

The optical assembly can include a first cycloidal diffractive waveplate and a second cycloidal diffractive waveplate, the first cycloidal diffractive waveplate receiving a normally incident optical beam having a polarization volume grating structure providing high diffraction efficiency at a selected operating wavelength of the beam steering system, and components so that the rotational positions of the first and the second cycloidal diffractive waveplates are independently controlled by the controller assembly.

The optical assembly can include a first set of N non-switchable cycloidal diffractive waveplates, all of which include lines of constant optical anisotropy axis orientation, the lines being parallel to each other both over an entire area of each non-switchable cycloidal diffractive waveplate, and among all members of the first set of N non-switchable cycloidal diffractive waveplates, each member of the first set of N non-switchable cycloidal diffractive waveplates being preceded along a path of optical radiation propagating through the beam steering system by a switchable polarization converter that in one state converts left-hand circularly-polarized optical radiation to right-hand circularly-polarized optical radiation, and right-hand circularly-polarized optical radiation to left-hand circularly polarized optical radiation, and in the other state passes optical radiation without changing its polarization, and the number N being a positive integer equal to or greater than one.

The optical system can further include a second set of N non-switchable cycloidal diffractive waveplates, all of which include lines of constant optical anisotropy axis orientation, the lines being parallel to each other both over an entire area of each non-switchable cycloidal diffractive waveplate of the second set of N non-switchable cycloidal diffractive waveplates, and between each member of the second set of N non-switchable cycloidal diffractive waveplates, the lines of constant optical anisotropy axis orientation in the second set of non-switchable cycloidal diffractive waveplates being orthogonal to the lines of constant optical anisotropy axis orientation in the first set of non-switchable cycloidal diffractive waveplates, and each member of the second set of N non-switchable cycloidal diffractive waveplates being preceded along a path of optical radiation propagating through the optical assembly of the beam steering system by a switchable polarization converter that in one state converts left-hand circularly-polarized optical radiation to right-hand circularly-polarized optical radiation, and right-hand circularly-polarized optical radiation to left-hand circularly polarized optical radiation, and in the other state passes optical radiation without changing its polarization.

A preferred embodiment of a lens system can include at least one diffractive waveplate lens having three functional layers, in all of which an optical anisotropy axis is parallel to a surface of at least one diffractive waveplate lens, in outer two layers of at least one of the diffractive waveplate lenses, the optical anisotropy axis orientation varying linearly with position in a direction perpendicular to a surface of the diffractive waveplate lenses, in an inner layer of at least one diffractive waveplate lens, the optical anisotropy axis orientation having no variation with position in a direction perpendicular to a surface of at least one cycloidal diffractive waveplate lens, and a twist angle of the optical anisotropy axis orientation in one of the two outer layers of at least one of the diffractive waveplate lens being equal in magnitude and opposite in sign to a twist angle of the optical anisotropy axis orientation of the other outer layer of at least one diffractive waveplate lens.

The lens system can further include a product of thickness and birefringence of the outer two layers of at least one cycloidal diffractive waveplate lens being about 30% of a selected operating wavelength of the lens system, a product of thickness and birefringence of the inner layer of at least one cycloidal diffractive waveplate lens being about 63% of the selected operating wavelength of the lens system, and an absolute value of an angle through which the optical anisotropy axis twists in the two outer layers of at least one cycloidal diffractive waveplate lens being about 82 degrees.

Further objects and advantages of this invention will be apparent from the following detailed description of the presently preferred embodiments which are illustrated schematically in the accompanying drawings.

BRIEF DESCRIPTION OF THE DRAWINGS

The drawing figures depict one or more implementations in accord with the present concepts, by way of example only, not by way of limitations. In the figures, like reference numerals refer to the same or similar elements.

DETAILED DESCRIPTION OF THE INVENTION

Figure 1:
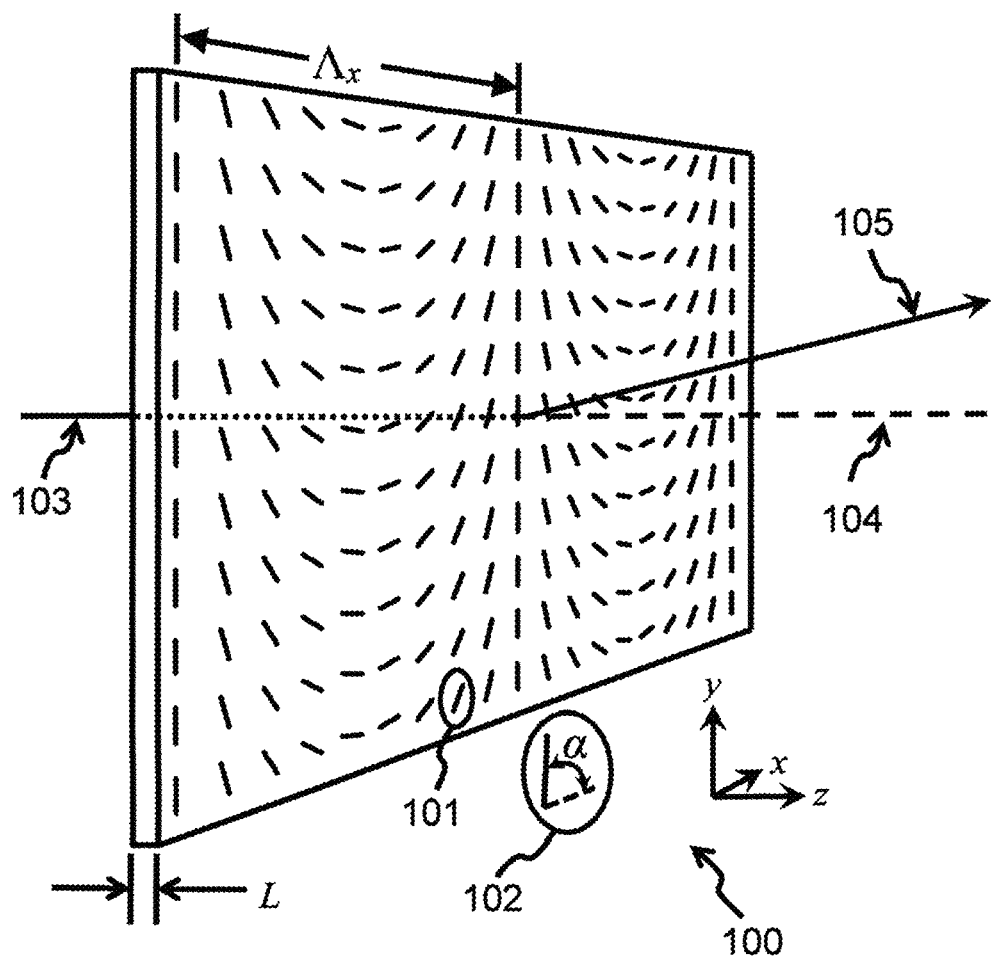
FIG. 1 shows a perspective view of the structure of a regular CDW, using the prior art.

Before explaining the disclosed embodiments of the present invention in detail, it is to be understood that the invention is not limited in its applications to the details of the particular arrangements shown since the invention is capable of other embodiments. Also, the terminology used herein is for the purpose of description and not of limitation.

In the Summary of the Invention above and in the accompanying drawings, reference is made to particular features of the invention. It is to be understood that the disclosure of the invention in this specification does not include all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

In this section, some embodiments of the invention will be described more fully with reference to the accompanying drawings, in which preferred embodiments of the invention are shown. This invention can, however, be embodied in many different forms and should not be construed as limited to the embodiments set forth herein. Rather, these embodiments are provided so that this specification will be thorough and complete, and will convey the scope of the invention to those with ordinary skill in the art.

Other technical advantages may become readily apparent to one of ordinary skill in the art after review of the following figures and description.

It should be understood at the outset that, although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described below.

Unless otherwise specifically noted, articles depicted in the drawings are not necessarily drawn to scale.

The term "optical radiation" sometimes refers to electromagnetic radiation with a wavelength in the visible spectrum, nominally between approximately 400 nm and approximately 700 nm. For convenience, the term "optical radiation" will be used in this disclosure to more generally refer to electromagnetic radiation at any wavelength. Some of the examples of the invention described herein are for wavelengths within the visible spectrum, but the invention applies to other bands of electromagnetic radiation as well, limited only by the availability of materials that are transparent and anisotropic in these other bands, and for which methods of forming the required patterns of optical anisotropy axis orientation are available, or can be made available.

In this disclosure, the term "beam steering system" will be used to describe systems designed to steer an optical beam, for example a laser beam. It is to be understood that all of the beam steering systems described herein have the capability to steer the field of view of an imaging system, and that the methods for increasing the efficiency of beam steering systems disclosed herein apply equally to field of view steering systems.

A listing of components will now be described:

100 Regular CDW, having no variation in the optical anisotropy axis orientation along the direction perpendicular to the surface of the CDW.

101 Line segment indicating local orientation of the optical anisotropy axis of the anisotropic material comprising the regular CDW.

102 Diagram indicating the angle $\alpha$ between the x axis and the local orientation of the optical anisotropy axis of the anisotropic material comprising the regular CDW.

103 Direction of propagation of a plane wave optical beam normally incident on a regular CDW.
104 Continuation of the direction of propagation of a plane wave optical beam if it had not been diffracted by the regular CDW.
105 Direction of propagation of a plane wave optical beam diffracted by the regular CDW.
201 An illustration of the optical anisotropy axis orientation at a first plane in a CDW. The illustrated first plane is parallel to the surface of the CDW of which the plane is a part. In the illustrated plane, the optical anisotropy axis orientation varies in a direction perpendicular to the surface of the CDW. The angle between the optical anisotropy axis and the x axis in the lower left corner of the first plane is 0.
202 An illustration of the optical anisotropy axis orientation at a second plane in a CDW. The illustrated second plane is parallel to the surface of the CDW of which the plane is a part. In the illustrated plane, the optical anisotropy axis orientation varies in a direction perpendicular to the surface of the CDW. The angle between the optical anisotropy axis and the x axis in the lower left corner of the second plane is approximately 30°.
203 An illustration of the optical anisotropy axis orientation at a third plane in a CDW. The illustrated third plane is parallel to the surface of the CDW of which the plane is a part. In the illustrated plane, the optical anisotropy axis orientation varies in a direction perpendicular to the surface of the CDW. The angle between the optical anisotropy axis and the x axis in the lower left corner of the third plane is approximately 60°.
204 An illustration of the optical anisotropy axis orientation at a fourth plane in a CDW. The illustrated fourth plane is parallel to the surface of the CDW of which the plane is a part. In the illustrated plane, the optical anisotropy axis orientation varies in a direction perpendicular to the surface of the CDW. The angle between the optical anisotropy axis and the x axis in the lower left corner of the fourth plane is approximately 90°.
300 Four combined planes of a CDW in which the optical anisotropy axis orientation varies along the direction perpendicular to the surface of the CDW.
301 An illustration of the optical anisotropy axis orientation at a first plane in a CDW which has the property that the optical anisotropy axis orientation varies in a direction perpendicular to the surface of the CDW. The angle between the optical anisotropy axis and the x axis in the lower left corner of the first plane is 0.
302 An illustration of the optical anisotropy axis orientation at a second plane in a CDW which has the property that the optical anisotropy axis orientation varies in a direction perpendicular to the surface of the CDW. The angle between the optical anisotropy axis and the x axis in the lower left corner of the second plane is approximately 30°.
303 An illustration of the optical anisotropy axis orientation at a third plane in a CDW which has the property that the optical anisotropy axis orientation varies in a direction perpendicular to the surface of the CDW. The angle between the optical anisotropy axis and the x axis in the lower left corner of the third plane is approximately 60°.
304 An illustration of the optical anisotropy axis orientation at a fourth plane in a CDW which has the property that the optical anisotropy axis orientation varies in a direction perpendicular to the surface of the CDW. The angle between the optical anisotropy axis and the x axis in the lower left corner of the fourth plane is approximately 90°.
305 The optical beam incident on the CDW parallel to the z axis with optical anisotropy axis orientation that varies in a direction perpendicular to the CDW.
306 The optical beam at the output of the CDW, with a direction of propagation that has been altered due to diffraction from the CDW.
400 CDW with twist-uniform-twist (TUT) structure, illustrating the variation of the orientation of the molecules of the anisotropic material comprising the TUT CDW along the x axis, parallel to the surface of the CDW, and along the z axis, perpendicular to the surface of the CDW.
401 First layer of the TUT CDW, in which the optical anisotropy axis rotates counterclockwise for increasing value of the z coordinate, as viewed looking in the positive z direction.
402 Second layer of the TUT CDW, in which the optical anisotropy axis orientation is independent of the z coordinate.
403 Third layer of the TUT CDW, in which the optical anisotropy axis rotates clockwise for increasing value of the z coordinate, as viewed looking in the positive z direction.
600 A schematic of the optical assembly of a beam steering system, the active beam steering components consisting of two CDWs whose rotational position can be independently controlled in order to vary the pointing direction of the output beam.
601 The first CDW encountered by plane wave optical beam incident on the optical assembly of the beam steering system.
602 The second CDW encountered by plane wave optical beam incident on the optical assembly of the beam steering system.
603 The plane wave optical beam incident on the optical assembly of the beam steering system.
604 The plane wave optical beam at the output from the optical assembly of the beam steering system, with a direction of propagation that has been altered by passage through that assembly.
701 The first switchable polarization converter encountered by a plane wave optical beam propagating from left to right parallel to the z axis in the figure. The switchable polarization converter can be switched by application of an electrical waveform across the active liquid crystal layer that is part of the switchable polarization converter.
702 The first CDW that is encountered by a plane wave optical beam propagating from left to right in the figure.
703 The second switchable polarization converter encountered by a plane wave optical beam propagating from left to right in the figure. The switchable polarization converter can be switched by application of an electrical waveform across the active liquid crystal layer that is part of the switchable polarization converter.
704 The second CDW that is encountered by a plane wave optical beam propagating from left to right in the figure.
800 The optical assembly of a beam steering system, the optical assembly comprising two switchable polarization converters and two CDWs, a plane wave optical beam incident from the left side of the figure and exiting on the right side of the figure.
801 The first switchable polarization converter encountered by a plane wave optical beam propagating from left to right parallel to the z axis in the figure. The switchable polarization converter can be switched by application of an electrical waveform across the active liquid crystal layer that is part of the switchable polarization converter.

802 The first CDW that is encountered by a plane wave optical beam propagating from left to right in the figure.

803 The second switchable polarization converter encountered by a plane wave optical beam propagating from left to right in the figure. The switchable polarization converter can be switched by application of an electrical waveform across the active liquid crystal layer that is part of the switchable polarization converter.

804 The second CDW that is encountered by a plane wave optical beam propagating from left to right in the figure.

805 The plane wave optical beam that is incident on the optical assembly of the beam steering system. The incident plane wave optical beam propagates in a direction parallel to the z axis.

806 The plane wave optical beam that exits the optical assembly of the beam steering system, the optical beam having been diffracted into a direction different from its direction of propagation at the input.

1300 A beam steering system that includes both an optical assembly and a controller assembly. The system allows adjustment of the angle through which an input optical beam is deflected.

1301 The optical assembly of the beam steering system, containing CDWs for diffracting the optical beam.

1302 The controller assembly that commands the optical assembly of the beam steering system, thereby causing the optical beam to be pointed in a desired direction.

1303 The signal connections between the controller assembly and the optical assembly of the beam steering system. This connection could be implemented by an electrical cable or by wireless means.

1304 The optical beam incident on the optical assembly of the beam steering system.

1305 The optical beam exiting from the optical assembly, after having been steered to a desired pointing direction.

1401 A diffractive waveplate lens or lens system with TUT structure, focusing a beam incident at a steep angle of incidence.

1402 An input optical beam incident on the lens or lens system at a steep angle of incidence.

1403 The input optical beam after being diffracted by the diffractive waveplate lens.

1404 The point at which the output beam comes to a focus.

Diffractive waveplates are known and have found many uses in optical systems. Cycloidal diffractive waveplates (CDWs) are shown and described in U.S. Pat. Nos. 9,557,456, 9,658,512, 9,715,048, and 10,036,886 to Tabirian et al., which are all assigned to the same assignee as the subject patent application, and which are all incorporated by reference in their entirety.

Detailed methods of fabricating diffractive waveplates have been disclosed in U.S. Pat. Nos. 9,617,205, 9,983,479, and 10,031,424 to Tabirian et al., which are also all assigned to the same assignee as the subject patent application, and which are all incorporated by reference in their entirety.

Diffractive waveplate lenses are shown and described in U.S. Pat. Nos. 9,753,193, 10,114,239, 10,120,112, 10,191,191, 10,197,715, 10,274,650, and 10,274,805 to Tabirian et al., and U.S. patent application Ser. No. 16/169,717 filed Oct. 24, 2018 to Tabirian et al. (U.S. Published Patent Application 2019/0113777), which are also all assigned to the same assignee as the subject patent application, and which are all incorporated by reference in their entirety.

In this disclosure, the expression "regular CDW" will be used to mean a CDW in which the spatial dependence of the optical anisotropy axis orientation of the birefringent material comprising the regular CDW can be described by the following formula:

$$\hat{n}_R = \hat{y}\,\sin\!\left[\frac{\pi x}{\Lambda_x} + C\right] + \hat{x}\,\cos\!\left[\frac{\pi x}{\Lambda_x} + C\right] \qquad (\mathrm{I})$$

Here $\hat{n}_R$ is a unit vector pointing along the extraordinary axis of the birefringent material, $\hat{x}$ and $\hat{y}$ are unit vectors pointing along x and y Cartesian coordinate axes, respectively, $\Lambda_x$ is the period of the CDW, and C is a constant. The surfaces of this regular CDW are perpendicular to the z axis.

In this disclosure, the expression "regular diffractive waveplate lens" will be used to mean a diffractive waveplate lens in which the spatial dependence of the optical anisotropy axis orientation can be locally approximated by formula (I), where the coordinate system is adjusted so that the radial direction, that is, the direction away from the center of the lens, is along the x axis. For a diffractive waveplate lens, the period is inversely proportional to distance from the center of the lens.

As described in the above-enumerated U.S. patents, and as is well known in the art, the diffraction efficiency of regular CDWs approaches approximately 100% when $\theta_I \ll \pi/2$, where $\theta_I$ is the angle of incidence, and $\Lambda_x \gg \lambda$, where $\lambda$ is the wavelength, provided that the half-wave condition $L\Delta n = \lambda/2$ is satisfied, where L is the thickness of the regular CDW and $\Delta n$ is the birefringence of the anisotropic material comprising the CDW. Therefore, for steering systems that steer optical beams at a specific wavelength through small angles, with small angles of incidence, high diffraction efficiency can be obtained by employing regular CDWs as components of the beam steering system. It is an objective of this disclosure to relieve this small-angle constraint on the diffraction angles and angles of incidence attainable with beam steering and field of view steering systems.

As described in the above-enumerated U.S. patents, and as is well known in the art, the diffraction efficiency of regular diffractive waveplate lenses approaches approximately 100% when $\theta_I \ll \pi/2$, where $\theta_I$ is the angle of incidence, and the local period is much greater than the wavelength over the entire area of the lens, provided that the half-wave condition $L\Delta n = \lambda/2$ is satisfied, where L is the thickness of the regular diffractive waveplate lens and $\Delta n$ is the birefringence of the anisotropic material comprising the lens. The maximum angle of diffraction is small for lenses with large f-number, and the maximum angle of diffraction is large for lenses with small f-number. Therefore, for diffractive waveplate lenses with sufficiently large f-number, with small angles of incidence, high diffraction efficiency can be obtained. It is an objective of this disclosure to relieve these constraints on angle of incidence and f-number that are required in order to obtain high diffraction efficiency in diffractive waveplate lenses fabricated in accordance with prior art.

FIG. 1 illustrates the optical anisotropy axis orientation pattern in one plane of a regular CDW 100. The short line segments 101 in FIG. 1 represent the local orientation of the optical anisotropy axis of the birefringent material. This orientation satisfies formula (I), in that the orientation direction depends only on the x coordinate, and not on the y or z coordinates. From formula (I), the angle α that the local optical anisotropy axis makes with the x axis, shown at 102, is given by $\alpha = \pi x/\Lambda_x + C$. As noted previously, the diffraction efficiency of such a CDW will approach 100% if the thickness L of the regular CDW is such that L$\Delta$n=$\lambda$/2 at the wavelength $\lambda$ of the incident beam, the beam 103 is incident at an angle $\theta_I$<<$\pi$/2, and the period $\Lambda_x$ satisfies $\Lambda_x$>>$\lambda$. The direction that the input beam would propagate in the absence of the CDW is shown as 104, and the direction of propagation of the diffracted beam is shown as 105. For practical CDWs, the thickness L is generally orders of magnitude smaller than the lateral dimensions of the CDW. For example, for a typical CDW made from liquid crystal polymer (LCP), designed for operation in the visible spectral region, the thickness L is typically less than 2 micrometers, whereas the lateral dimensions of the CDW, along the x and y coordinates in FIG. 1, are typically in the range of tens to hundreds of millimeters. Thus, such CDWs are typically fabricated as coatings on a supporting transparent optical substrate.

Figure 2:
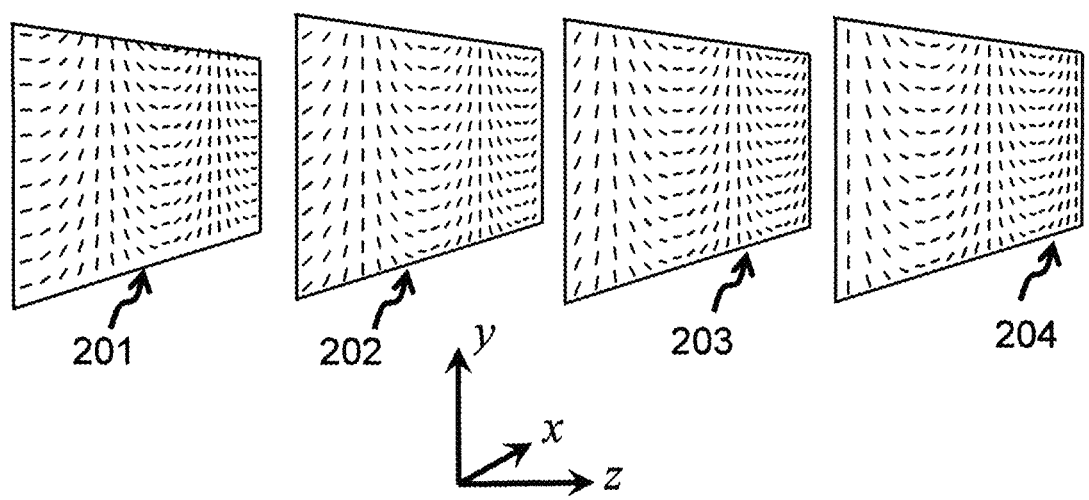
FIG. 2 shows a perspective view of the optical anisotropy axis orientation in four different planar layers of a CDW, with a different optical anisotropy axis orientation pattern in each of the four layers, using the prior art. For purposes of illustration, the layers have been separated so the optical anisotropy axis pattern of each layer is visible.

Within the thickness L of a regular CDW or a regular diffractive waveplate lens, the optical anisotropy axis does not depend on the z coordinate, which for our purposes here is the direction perpendicular to the film comprising the regular CDW or regular diffractive waveplate lens. It has been found that structures in which the optical anisotropy axis orientation does vary along the z axis in a particular way have broader spectral bandwidth than regular CDWs. Therefore, such CDWs are described as achromatic CDWs. An example of variation of optical anisotropy axis orientation along the z axis, i.e. along the axis perpendicular to the surface of a layer within a CDW, is shown in FIG. 2. In this figure, four different planes of a layer within a CDW are shown, with the distance between planes greatly expanded for purposes of illustration in order to reveal the optical anisotropy axis structure. In plane 201, the optical anisotropy axis in the lower left corner is parallel to the x axis. In plane 202, the optical anisotropy axis in the lower left corner makes an angle of approximately 30° with the x axis. In plane 203, the optical anisotropy axis in the lower left corner makes an angle of approximately 60° with the x axis. In plane 204, the optical anisotropy axis in the lower left corner makes an angle of approximately 90° with the x axis.

Figure 3:
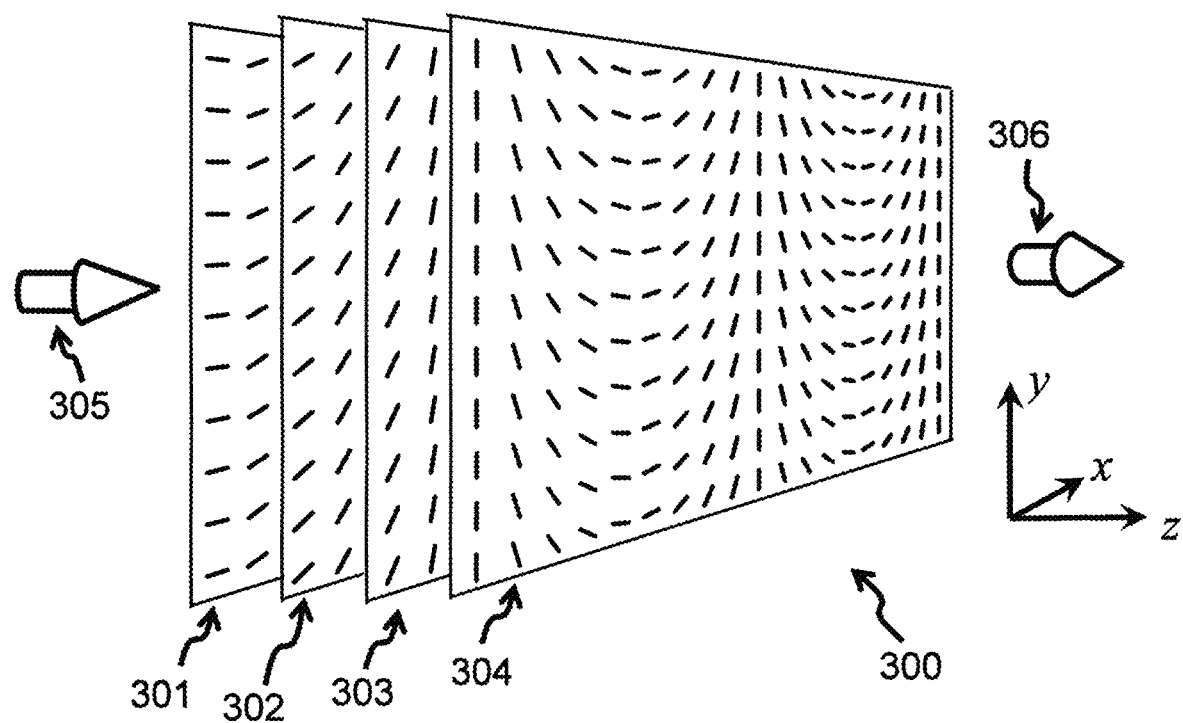
FIG. 3 shows a perspective view of the optical anisotropy axis orientation in four different planar layers of a CDW, with a different optical anisotropy axis orientation in each of the four layers, using the prior art. The layers are shown closely spaced, as in an actual CDW with optical anisotropy axis pattern continuously varying in the direction perpendicular to the surface of the CDW.

FIG. 3 shows the four planes of FIG. 2 collapsed into a compact layer 300 in which the optical anisotropy axis orientation varies linearly in both the x and z directions. In plane 301, the optical anisotropy axis in the lower left corner is parallel to the x axis. In plane 302, the optical anisotropy axis in the lower left corner makes an angle of approximately 30° with the x axis. In plane 303, the optical anisotropy axis in the lower left corner makes an angle of approximately 60° with the x axis. In plane 304, the optical anisotropy axis in the lower left corner makes an angle of approximately 90° with the x axis. The resulting composite of all the planes has a twisted structure, in that the optical anisotropy axis twists along the z axis. The optical anisotropy axis pattern of twisted layer 300 can be described as follows:

$$\hat{n}_T = \hat{y} \sin\left[\frac{\pi x}{\Lambda_x} + \frac{\pi s z}{\Lambda_z} + C'\right] + \hat{x} \cos\left[\frac{\pi x}{\Lambda_x} + \frac{\pi s z}{\Lambda_z} + C'\right] \quad \text{(II)}$$

In formula (II), $\hat{n}_T$ is a unit vector pointing along the extraordinary axis of the birefringent material layer with twisted structure, $\hat{x}$ and $\hat{y}$ are unit vectors pointing along the x and y Cartesian coordinate axes, respectively, and C' is a constant. The sign parameter s=+1 or −1, depending on the chirality of the twist. The parameters $\Lambda_x$ and $\Lambda_z$ are the periods over which the optical anisotropy axis orientation changes by pi radians (180°) along the x and z axes, respectively. The angle $\alpha$ that the local optical anisotropy axis makes with the x axis is therefore $\alpha$=$\pi$x/$\Lambda_x$+$\pi$sz/$\Lambda_z$+C'. The diffraction of optical radiation by the twisted structure 300 is illustrated by an optical beam 305 propagating parallel to the z axis, normally incident on the structure, and by an output beam 306 whose direction of propagation has been altered by passage through the structure 300.

Figure 4:
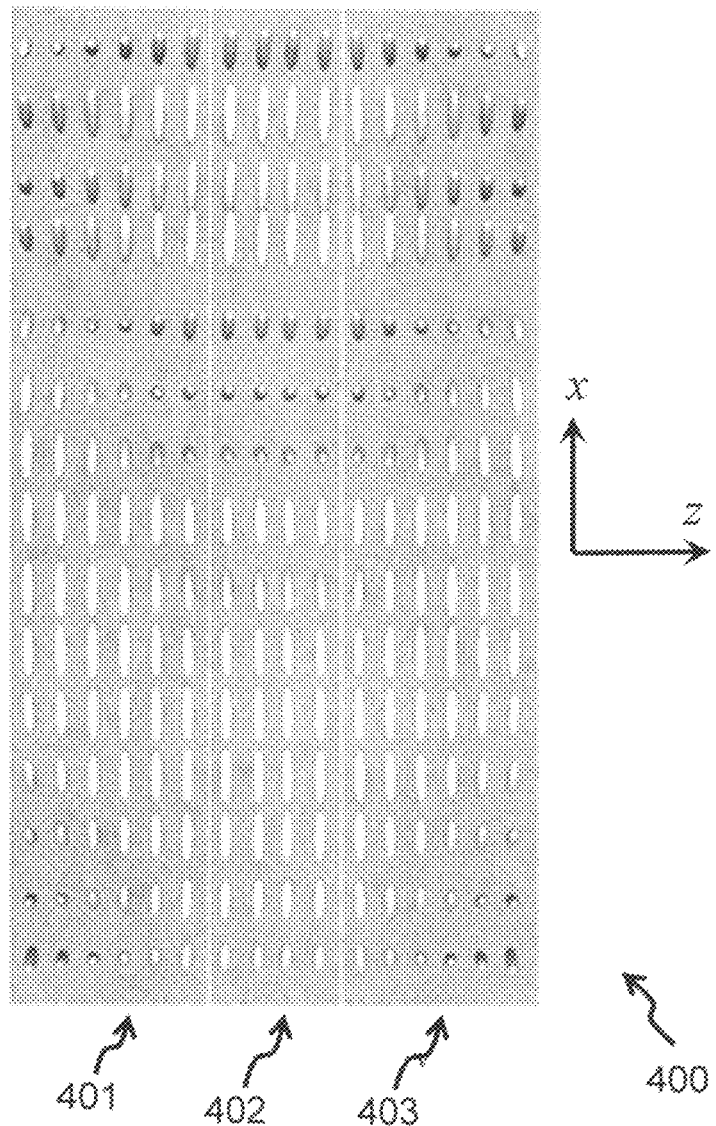
FIG. 4 illustrates the orientation of molecules of an anisotropic material in a TUT CDW, using the prior art. The macroscopic optical director axis of such a CDW is parallel to the long axis of the molecules at every location within the CDW.

FIG. 4 illustrates a three-layer CDW 400 in which the optical anisotropy axis orientation has the same period in the x direction in all three layers 401, 402, and 403. In FIG. 4, the local optical anisotropy axis direction is represented by the long axes of oblate spheroids. The optical anisotropy axis orientation is independent of the z axis coordinate in the central layer 402, but it depends on the z axis coordinate in the two outer layers 401 and 403. We will refer to such a structure as is illustrated in FIG. 4 as a twist-uniform-twist (TUT) CDW. With appropriate values of the thickness of the three layers 401, 402, and 403, and the angles through which the optical anisotropy axis twists in the two outer layers 401 and 403, this structure has been shown both experimentally and theoretically to have a wider spectral bandwidth than the regular CDW illustrated, for example, in FIG. 1. Structures having the appropriate values of thickness and twist angles are therefore referred to as achromatic CDWs.

Currently available methods of fabrication of CDWs, such as spin-coating of multiple layers of liquid crystal monomer, require that the optical anisotropy axis orientation be continuous throughout the structure. The TUT structure shown in FIG. 4 has this property throughout its structure. More specifically, the optical anisotropy axis orientation has no spatial discontinuities. In particular, the optical anisotropy axis orientation is continuous across the interface between layer 401 and layer 402, as well as across the interface between layer 402 and layer 403. To obtain a twisted structure in which the optical anisotropy axis orientation changes along the z coordinate, as in layers 401 and 403, a liquid crystal monomer with an added chiral dopant is used. Because the sign of the twist is opposite in layers 401 and 403, dopants of opposite chirality are used in fabricating these layers. A liquid crystal monomer with no chiral dopant is used to fabricate layer 402, within which there is no variation in optical anisotropy axis orientation along the z axis.

We will refer in this disclosure to the direction parallel to the z axis in FIG. 1, FIG. 2, FIG. 3, and FIG. 4, and perpendicular to the surface of the CDW or layer of a CDW, as the axial direction.

Figure 5:
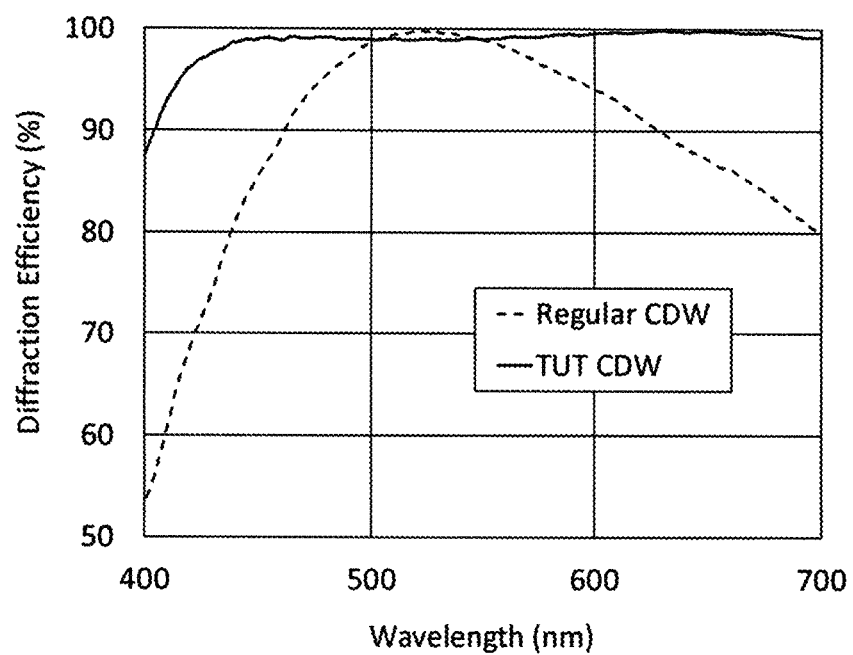
FIG. 5 shows the measured diffraction efficiency as a function of wavelength for a regular CDW and a TUT CDW, fabricated using the prior art.

FIG. 5 shows the measured diffraction efficiency of both a regular CDW and a TUT CDW as a function of wavelength. These CDWs were fabricated from liquid crystal monomers, which were then polymerized to form liquid crystal polymer (LCP). As expected, based on modeling and simulation, FIG. 5 shows that the fabricated TUT CDW maintains high diffraction efficiency over a broader band of wavelengths than the regular CDW.

The optical anisotropy axis pattern of the regular CDW for which experimental diffraction efficiency results are shown in FIG. 5 is given by formula (I) above, with $\Lambda_x$ approximately equal to 5 µm and C having an arbitrary value dependent on the choice of the origin of the Cartesian coordinate system. The thickness of the CDW is its extent along the z axis, determined by the half-wave condition L$\Delta$n=$\lambda$/2 for a wavelength of $\lambda$=approximately 550 nm. The birefringence of the LCP used to fabricate the regular CDW for which diffraction efficiency is shown in FIG. 5 was $\Delta$n approximately equal to 0.16, implying a CDW thickness of L approximately equal to approximately 1.72 μm.

The optical anisotropy axis pattern of the first layer of the TUT CDW for which experimental diffraction efficiency results are shown in FIG. 5 is given by formula (II) above, with $\Lambda_x$ approximately equal to 5 μm and $\Lambda_z$ approximately equal to 2.26 μm. In order to define the optical anisotropy axis pattern throughout the TUT CDW, we may choose a value of C'=0 in formula (I). The thickness of the first layer of the CDW is equal to approximately 1.03 μm, so the value of coordinate z varies from 0 to approximately 1.03 μm within the first layer. The TUT CDW can be fabricated with the same LCP as is used to fabricate the regular CDW, except for the addition of a small amount of chiral dopant required to produce the twisted structure of the two outer layers, so the birefringence Δn of the LCP in all three layers of the TUT CDW may be equal to approximately 0.16.

FIG. 4 can be used to visualize the structure of the TUT CDW for which measured diffraction efficiency is shown in FIG. 5. For convenience, we define coordinate z to be zero on the left side of the three-layer structure shown in FIG. 4. Since the thickness of the first layer 401 is approximately 1.03 μm, the boundary between the first layer 401 and the second layer 402 occurs at z approximately equal to 1.03 μm.

The optical anisotropy axis pattern of the second layer 402 of the TUT CDW for which experimental diffraction efficiency results are shown in FIG. 5 is given by formula (I) above, with $\Lambda_x$ approximately equal to 5 μm, the same as the period in the first layer. Due to the method of fabrication, the optical anisotropy axis orientation across the interfaces between the layers of the TUT CDW is continuous. This requires a particular value of C in formula (I) to describe the optical anisotropy axis orientation of the second layer 402. The constant can be determined by requiring that the optical anisotropy axis pattern given by formula (II) for the first layer at z approximately equal to 1.03 μm, at the boundary between the first layer 401 and the second layer 402, be the same as the optical pattern in the second layer at this boundary. This requires that the constant C in formula (I) describing second layer 402 is approximately equal to 82°.

A complete definition of the optical anisotropy axis orientation n̂ throughout the three layers of the TUT CDW is provided in the following formulas:

Layer 401, first layer, with twist:

$$\hat{n} = \hat{y}\,\sin\left[\frac{\pi x}{\Lambda_x} + \frac{\pi z}{\Lambda_z}\right] + \hat{x}\,\cos\left[\frac{\pi x}{\Lambda_x} + \frac{\pi z}{\Lambda_z}\right],\ 0 \leq z < z_1 \quad \text{(IV)}$$

Layer 402, second layer, without twist:

$$\hat{n} = \hat{y}\,\sin\left[\frac{\pi x}{\Lambda_x} + C\right] + \hat{x}\,\cos\left[\frac{\pi x}{\Lambda_x} + C\right],\ z_1 \leq z < z_2 \quad \text{(V)}$$

Layer 403, third layer, with twist:

$$\hat{n} = \hat{y}\,\sin\left[\frac{\pi x}{\Lambda_x} - \frac{\pi z}{\Lambda_z} + C'\right] + \hat{x}\,\cos\left[\frac{\pi x}{\Lambda_x} - \frac{\pi z}{\Lambda_z} + C'\right],\ z_2 \leq z \leq z_3 \quad \text{(VI)}$$

As indicated by the change in the sign of the term proportional to z in formula (VI) compared with the term proportional to z in formula (IV), the chirality of the twist in layer 403 is opposite to that of layer 401.

As noted previously, the periods along the x and z axes are $\Lambda_x$ approximately equal to 5 μm and $\Lambda_z$ approximately equal to 2.26 μm, respectively. The value of C in formula (V) is approximately equal to 82°, and the value of C' in formula (VI) is approximately equal to 336°. The values of $z_1$, $z_2$, and $z_3$ are approximately 1.03 μm, approximately 3.20 μm, and approximately 4.23 μm, respectively. These values assure the continuity of the optical anisotropy axis orientation across the boundaries between the layers.

Although the TUT design described by formulas (IV), (V), and (VI) results in a CDW that diffracts efficiently only in a wide band of wavelengths around the desired operating wavelength π=approximately 550 nm, the design can be adapted to a band centered around any other wavelength π' by simply multiplying the values of $\Lambda_x$, $\Lambda_z$, $z_1$, $z_2$, and $z_3$ listed above by λ'/λ. Small corrections to this rule may need to be made to account for dispersion of the indices of refraction of the birefringent material used to fabricate the TUT CDW, but these corrections can be readily determined by one with ordinary skill in the art.

For purposes of illustration, we employed a specific LCP formulation in the TUT CDW for which diffraction efficiency data is illustrated in FIG. 5. However, the results described in this disclosure are not confined to only this LCP formulation. In particular, CDWs of TUT structure with other values of birefringence Δn could be used with essentially the same results, provided only that the twist angles in the two outer layers of the TUT CDW are kept the same, and the product of layer thickness L and birefringence Δn are kept constant. To include this flexibility of material composition in the description of the design, the TUT CDW for which diffraction efficiency data is shown in FIG. 5 can be described by the following essential features:

Twist angles of about 82° magnitude in the outer two layers of the TUT structure, the twist angle of each of the outer layers having a sign opposite to that of the twist angle of the other of the outer layers;

the product of the thickness of each of the outer (twisted) layers and the birefringence of the LCP equal to about 30% of the desired operating wavelength;

the product of the thickness of the inner (non-twisted) layer and the birefringence of the LCP equal to about 63% the desired operating wavelength.

The desired operating wavelength of the TUT CDW for which diffraction efficiency measurement results are shown in FIG. 5 is approximately 550 nm. Therefore, according to the values given above, the product of the thickness of each of the twisted layers and the birefringence should be 0.30*(550 nm)=approximately 165 nm, and the product of the thickness of the untwisted layer and the birefringence should be approximately 0.63*(550 nm)=approximately 346.5 nm.

As noted previously, the specific TUT CDW for which diffraction efficiency measurements are shown in FIG. 5 has two outer layers each of which has a thickness of 1.03 μm. Since the birefringence of the LCP used to fabricate this CDW is Δn=approximately 0.16, the product of thickness and birefringence of the outer (twisted) layers is 165 nm, as expected. The thickness of the untwisted layer of the specific TUT CDW structure for which diffraction efficiency measurements are shown in FIG. 5 can be computed as $z_2 - z_1$=approximately 2.17 μm, so the product of the thickness of the inner (twisted) layer and the birefringence is approximately 346.5 nm within the numerical precision of the calculation.

Figure 6:
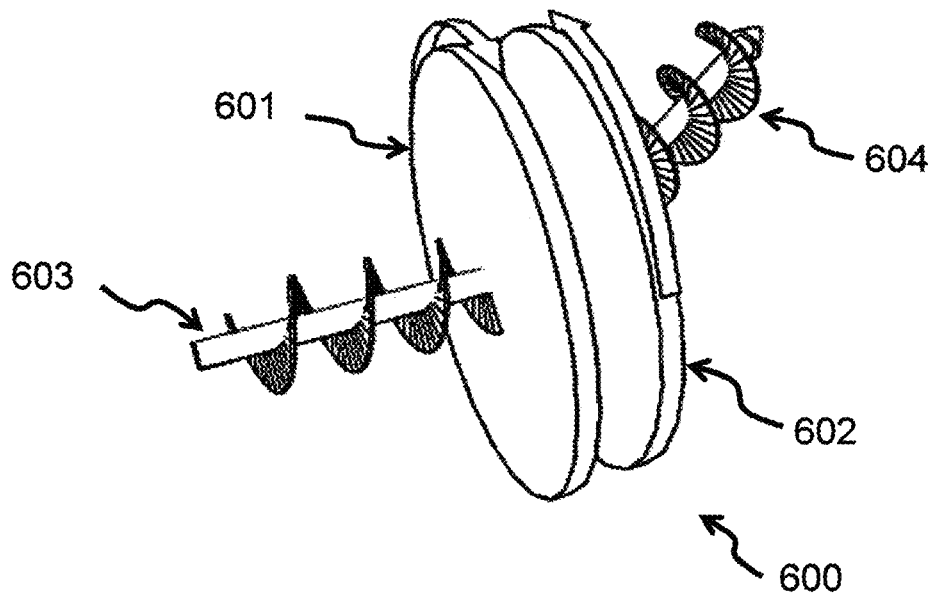
FIG. 6 illustrates the path of an optical beam through a beam steering system that includes two CDWs that can be rotated to adjust the pointing direction of the beam at the output of the beam steering system.

One of the configurations of the optical assembly of beam steering systems employing CDWs is illustrated in FIG. 6. By rotating CDW 601 and CDW 602 of optical assembly 600, an input beam propagating along direction 603 can be deflected into an output direction 604. The output direction can be continuously varied as the rotational positions of CDWs 601 and 602 are continuously varied. The spirals along directions 603 and 604 illustrate schematically the direction of the electric field of a circularly polarized input beam 603 and output beam 604. The configuration of the CDWs shown in FIG. 6 has been previously described in U.S. Pat. Nos. 9,557,456, 9,715,048, and 10,036,886 to Tabirian et al., which are each incorporated herein by reference in their entirety.

Figure 7:
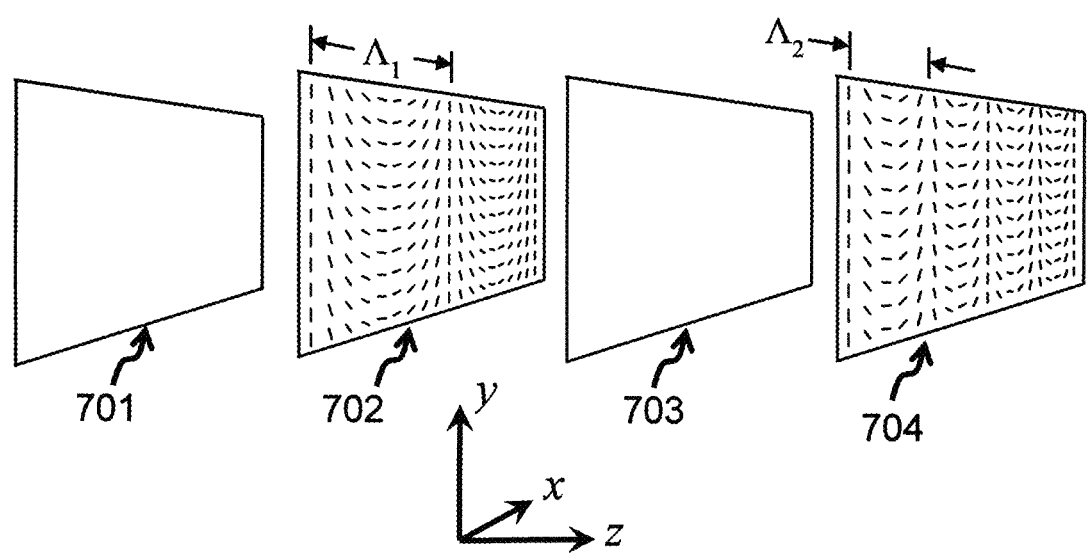
FIG. 7 shows a perspective view of four elements of a beam steering system consisting of switchable polarization converters interspersed with CDWs. The CDWs have different periods in order to provide a multiplicity of pointing directions, depending on the states of the switchable polarization converters. The four elements have been separated for purposes of illustration so that the optical anisotropy axis pattern of each element is visible, and the absence of any optical anisotropy axis pattern in the switchable polarization converters is also evident.
Figure 8:
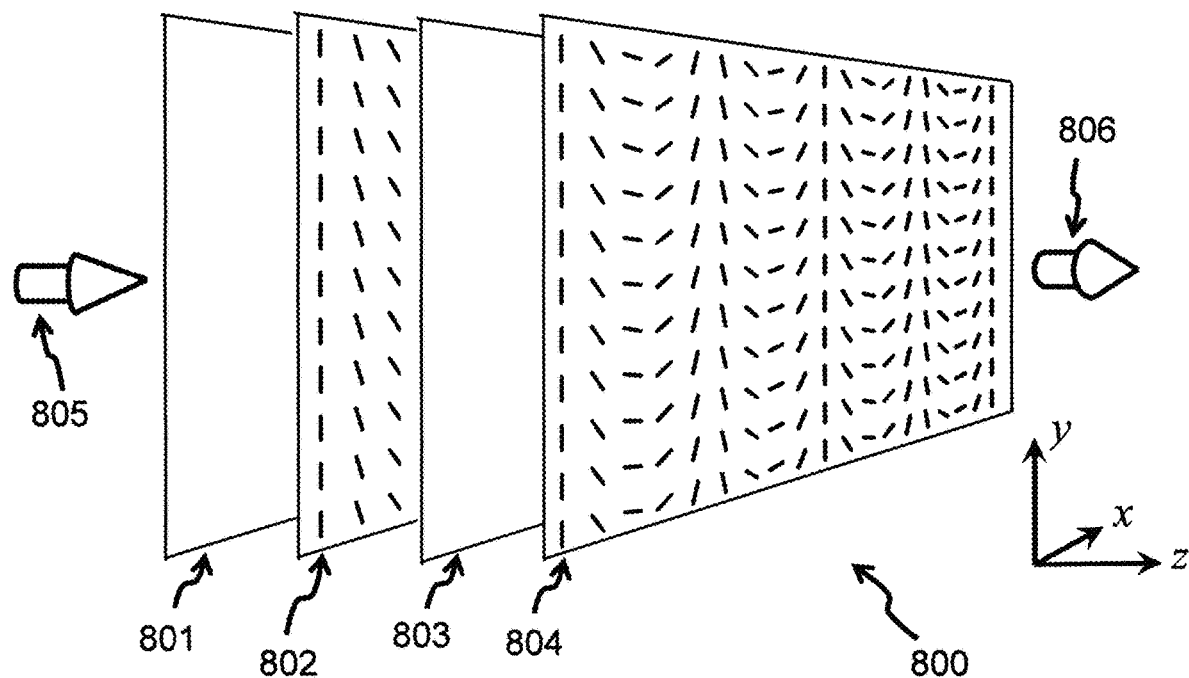
FIG. 8 shows a perspective view of four components of a beam steering system consisting of switchable polarization converters interspersed with CDWs. The components consist of two CDWs and two switchable polarization converters. The CDWs have different periods in order to provide a multiplicity of pointing directions, depending on the states of the switchable polarization converters. The four components are shown closely spaced, as in an actual beam steering system with multiple steering components.

A second configuration of the optical assembly of beam steering systems employing CDWs is illustrated in FIG. 7 and FIG. 8. In FIG. 7, the four components of the optical assembly of the beam steering system are spread out along the z axis in order to make it possible to view the optical anisotropy axis orientation of the CDWs 702 and 704. In FIG. 8, the same four components are shown more closely spaced, as they would be in an operational system. The components 701 and 703 in FIG. 7, and 801 and 803 in FIG. 8, are electronically-controlled switchable polarization converters that in one state, leave the circular polarization of transmitted optical radiation unchanged, and in the other state, change left-hand circularly polarized (LHCP) optical radiation to right-hand circularly-polarized (RHCP) optical radiation, and change RHCP optical radiation to LHCP optical radiation.

The non-switchable CDWs 702 and 704 in FIG. 7, and 802 and 804 in FIG. 8, deflect the optical radiation in different directions, depending on the polarization of the optical radiation incident on these CDWs. Therefore, changing the states of the switchable polarization converters allows any beam transmitted through the optical assembly of the beam steering system to be steered in different directions. As indicated in FIG. 7, the period $\Lambda_1$ of CDW 702 is twice the period $\Lambda_2$ of CDW 704. By switching the states of the polarization switches 701 and 703 in FIG. 7, and 801 and 803 in FIG. 8, the optical assembly 800 of the beam steering system can steer the beam or field of view to four different directions. An optical assembly with N sets of components, each set consisting of a switchable polarization converter and a CDW, can switch a beam or a field of view into $2^N$ directions. The optical assembly 800 of a beam steering system is an example of a beam steering system with N=2 such sets, resulting in the capability to point a beam or field of view in $2^N=4$ different directions.

The optical assembly 800 of FIG. 8 steers the beam into directions that are in the plane that includes the x and z axes. An additional N sets of components, each set consisting of a switchable polarization converter and a CDW, with CDWs that are the same as those of the first set but rotated approximately 90° about the z axis, would allow beam steering in the orthogonal direction. The overall system would therefore make it possible to steer a beam into a two-dimensional angular region.

Using prior art, the diffraction efficiency of beam steering systems such as those illustrated in FIG. 6 and FIG. 8 is reduced when the angle through which the system deflects optical radiation becomes large. The reason for this is illustrated in FIG. 9, which shows the measured diffraction efficiency of a regular CDW as a function of the angle of incidence, for the case in which the angle of incidence is in a plane perpendicular to the grating lines of the CDW.

Figure 9:
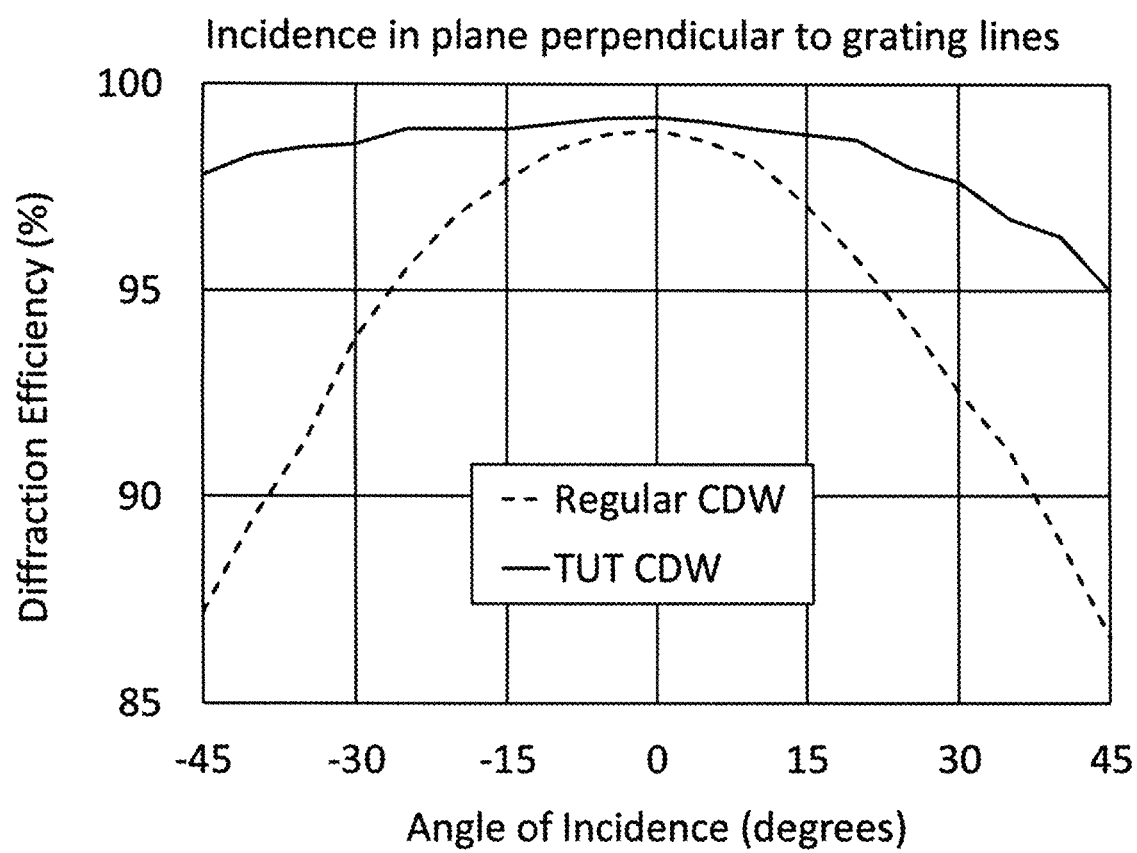
FIG. 9 shows the measured diffraction efficiency at a wavelength of 550 nm as a function of angle of incidence for a regular CDW and a TUT CDW. The angle of incidence is in a plane perpendicular to the lines of constant optical anisotropy axis orientation in the CDW.

Also shown in FIG. 9 is the measured diffraction efficiency of a TUT CDW for the same range of angles of incidence. It is clear from this figure that the measured diffraction efficiency for the TUT CDW is higher than for the regular CDW, especially at large angles of incidence. In any beam steering system that steers a beam over a large range of angles, the angles of incidence on at least some of the CDWs within the beam steering system will be large. Therefore, it follows from the experimental results of FIG. 9 that the overall diffraction efficiency of a beam steering system employing TUT CDWs will be higher than the overall diffraction efficiency of a beam steering system having the same angular range, but containing only regular CDWs.

Figure 10:
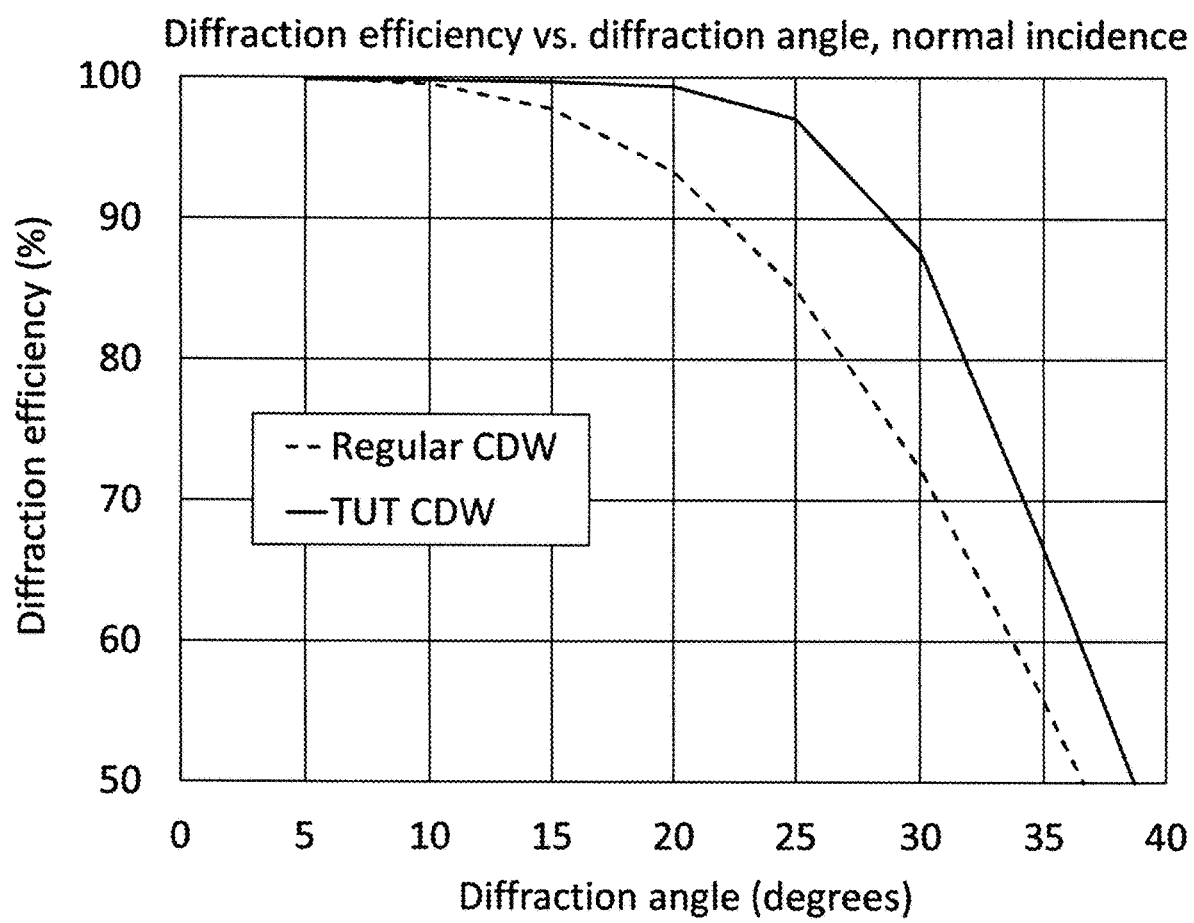
FIG. 10 shows the calculated diffraction efficiency of a regular CDW and a TUT CDW as a function of the angle through which an optical beam is diffracted, for a regular CDW and a TUT CDW, for an input with at normal incidence.

Beam steering systems and field-of-view steering systems that steer beams through a large angle, and lens systems with small f-number, require deflecting optical radiation through large angles. CDWs and diffractive waveplate lenses fabricated using prior art suffer significant reduction in diffraction efficiency when the diffraction angle becomes large. FIG. 10 illustrates the calculated diffraction efficiency of a CDW as a function of the angle through which an optical beam is diffracted, for normal incidence. It is evident from this figure that the TUT CDW has higher diffraction efficiency than the regular CDW, especially for large diffraction angles. The diffraction efficiency calculations illustrated in FIG. 10 also apply to diffractive waveplate lenses, in that the diffraction efficiency at any particular lateral position of a regular diffractive waveplate lens or a TUT diffractive waveplate lens depends on the diffraction angle at each particular lateral position, depending on the diffraction angle at each such particular position.

Figure 11:
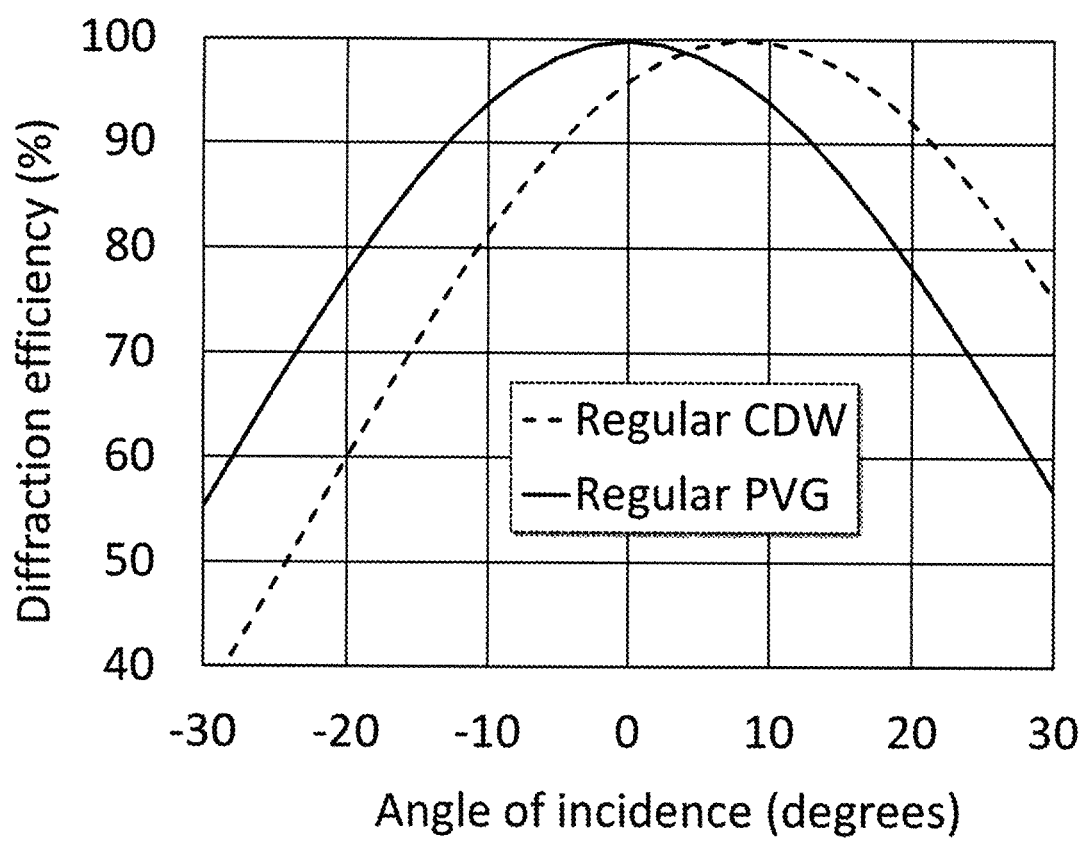
FIG. 11 shows the calculated diffraction efficiency of a circularly-polarized beam at normal incidence on a regular CDW and on a PVG, as a function of angle of incidence, for a beam with a propagation direction in a plane perpendicular to the lines of constant optical anisotropy axis orientation, with the regular CDW and PVG having a period such that they diffract the optical beam through an angle of 20°, of the prior art.

It is well known in prior art literature that CDWs having a particular structure referred to in the literature as that of a polarization volume grating (PVG) can be fabricated that have up to approximately 100% diffraction efficiency for a selected angle of incidence, angle of diffraction, and circular polarization. See D. Roberts, S. Kaim, N. Tabiryan, M. McConney, T. Bunning, "Polarization-Independent Diffractive Waveplate Optics," Proc. of IEEE Aerospace Conference (28 Jun. 2018), presented at the IEEE conference on Mar. 3-10, 2018, which is non-essential subject matter incorporated by reference in its entirety. The type of PVG described in the reference prior art publication will be referred to in this disclosure as a regular PVG to distinguish it from an alternative design. The calculated diffraction efficiency of a regular CDW and a regular PVG as a function of angle of incidence is illustrated in FIG. 11. For the calculation illustrated in FIG. 11, it was assumed that the optical beam was incident on the regular CDW and the regular PVG in a plane perpendicular to the lines of constant optical anisotropy axis orientation, the input radiation was circularly polarized, and the angle through which the regular CDW and the regular PVG diffracted normally incident light was 20°. The regular PVG was designed in accordance with prior art to have an efficiency of approximately 100% for normal incidence.

In beam steering systems such as the one illustrated in FIG. 6, the angle of incidence on the first CDW encountered by the steered beam (601 in FIG. 6) is zero and the input polarization can be fixed. Therefore, CDW 601 can be designed as a PVG with 100% diffraction efficiency, as illustrated in FIG. 11. The angle of incidence of the steered beam on CDW 602 in FIG. 6 will depend on the rotational position of both CDW 601 and CDW 602. As shown in FIG. 9, if the angle of incidence on CDW 602 is large, the diffraction efficiency will be higher if this CDW is TUT CDW than it would be if this CDW is a regular CDW.

In typical beam steering systems employing CDWs, the angles of incidence are as likely to be positive with respect to any given reference axis as they are to be negative. As illustrated in FIG. 11, the regular CDW has higher diffraction efficiency for positive angles of incidence than it does for negative angles of incidence. This asymmetry of the dependence of diffraction efficiency on angle of incidence would be a severe disadvantage in practical beam steering systems because it would result in low worst-case diffraction efficiency. This problem with use of regular CDWs can be illustrated by considering which of the two CDWs for which diffraction efficiency is shown in FIG. 11 would be most appropriate for use in the beam steering system illustrated in FIG. 6. Assuming that the diffractive element of the beam steering system is a regular PVG that diffracts the incident optical beam through an angle of 20° with an efficiency of approximately 100%, the angle of incidence on the second diffractive element could vary from −20° to +20°. According to FIG. 11, if the second diffractive element encountered by the optical beam is a regular CDW, the diffraction efficiency would vary between 60% for −20° angle of incidence and 92% for +20° angle of incidence. Also, according to FIG. 11, if the second diffractive element encountered by the optical beam is a regular PVG designed to have 100% efficiency at normal incidence, the diffraction efficiency would be at least 77% for all angles of incidence between −20° and +20°. Clearly, the worst-case diffraction efficiency is much higher for the regular PVG than for the regular CDW.

Figure 12:
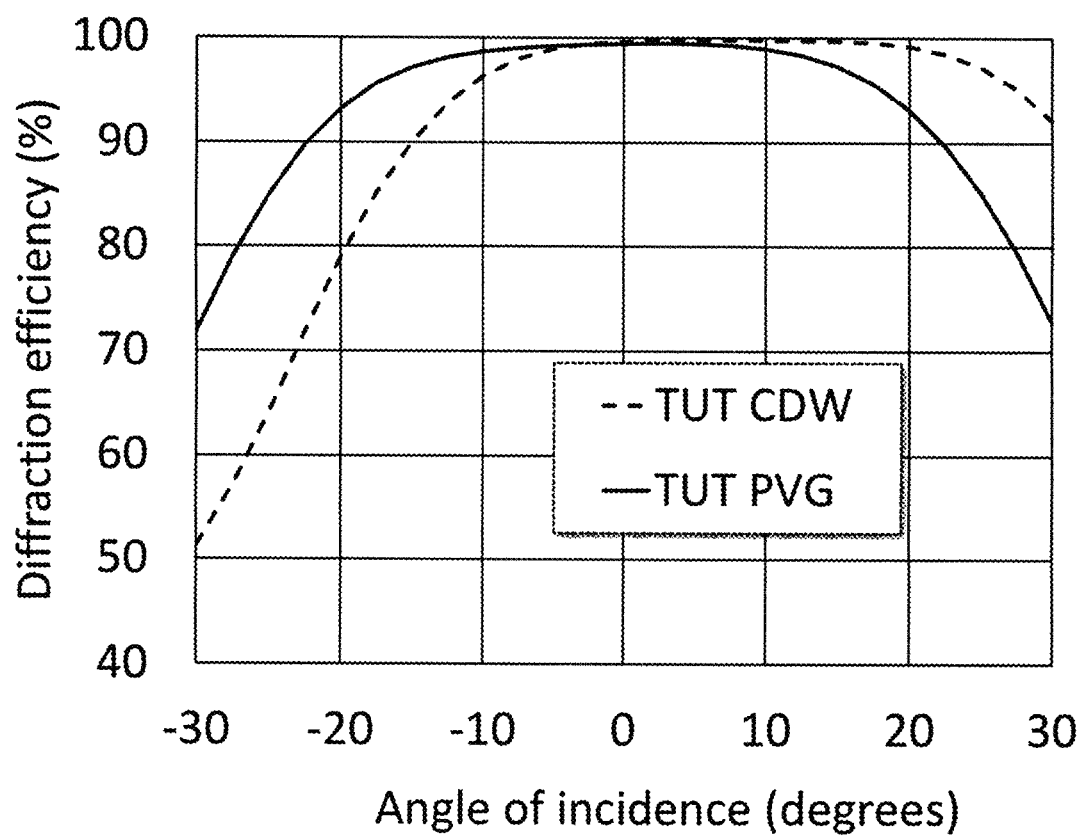
FIG. 12 shows the calculated diffraction efficiency of a circularly-polarized beam at normal incidence on a TUT CDW and on a TUT PVG, as a function of angle of incidence, for a beam with a propagation direction in a plane perpendicular to the lines of constant optical anisotropy axis orientation, with the TUT CDW and TUT PVG having a period such that they diffract the optical beam through an angle of 20°.

The calculated diffraction efficiency as a function of angle of incidence for two other types of diffractive waveplate are illustrated in FIG. 12. For the calculation illustrated in FIG. 12, it was assumed that the optical beam was incident on the TUT CDW and the TUT PVG in a plane perpendicular to the lines of constant optical anisotropy axis orientation, the input radiation was circularly polarized, and the angle through which the TUT CDW and the TUT PVG diffracted normally incident light was 20°. The first type of diffractive waveplate for which calculated diffraction efficiency is shown in FIG. 12 is a TUT CDW having the structure defined by formulas (IV), (V), and (VI). The second type of diffractive waveplate for which calculated diffraction efficiency is shown in FIG. 12 is a device that will be referred to here as a TUT PVG, which also has the structure defined by formulas (IV), (V), and (VI), except with the angles through which the orientation of the optical anisotropy axis in each layer adjusted so that the diffraction efficiency is the same for positive angles of incidence as it is for negative angles of incidence, as was done to convert the regular CDW to the PVG as illustrated in FIG. 11.

If the TUT CDW of FIG. 11 were used as the second diffractive element in FIG. 6, the lowest diffraction efficiency over the range of incident angles from −20° to +20° would be 79%. If the TUT PVG of FIG. 11 were used as the second diffractive element in FIG. 6, the lowest diffraction efficiency over the range of incident angles from −20° to +20° would be 93%. Clearly, either the worst-case diffraction efficiency is significantly higher when the second CDW in a beam steering system such as the one shown in FIG. 6 is a TUT CDW or a TUT PVG than if it is either a regular CDW or a regular PVG.

It was noted previously that the TUT CDW for which measured diffraction efficiency is shown in FIG. 5 and FIG. 9 could be characterized by a product of the thickness of the two twisted layers and the LCP birefringence being about 30% of the desired operating wavelength of approximately 550 nm, the product of the thickness of the untwisted layer and the LCP birefringence being about 63% of the desired operating wavelength, and the twist angles of the twisted layers being about 82°. To provide an indication of the allowable tolerances on these parameter values, the diffraction efficiency of such a TUT CDW was computed with changed values of all three of these parameters. The result of these calculations is that diffraction efficiency is still approximately 98.5% or higher with variations of these three parameter values by ±10% of their values.

Figure 13:
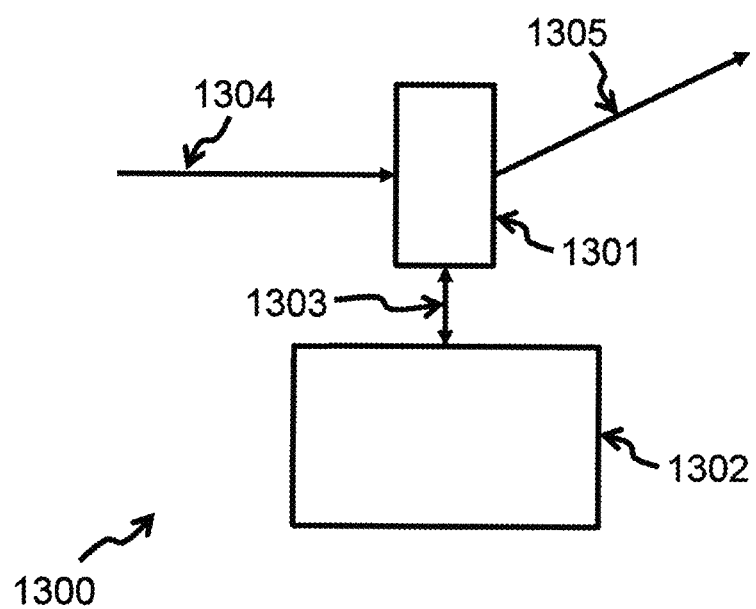
FIG. 13 is a schematic representation of a complete beam steering system, with an optical assembly that steers the beam or field of view, and a controller assembly that controls the angle through which the beam steering system steers the beam or field of view.

A complete beam steering system 1300 employing TUT CDWs or TUT PVGs is shown schematically in FIG. 13. An optical assembly 1301 contains the TUT CDWs or TUG PVGs and means to control them, which may include means to rotate them, as in FIG. 6, or means to switch the polarization of the optical radiation incident on them, as in FIG. 8. A controller assembly 1302 provides all needed signals and power to control the angle through which the optical assembly 1301 steers the beam.

The controller assembly 1302 can be connected to the optical assembly 1301 by means 1303 such as cables or a wireless connection. An input beam 1304 is deflected through a controllable angle into an output beam 1305 by the optical assembly 1301. FIG. 13 represents a complete field of view steering system if the direction of the arrows 1304 and 1305 are reversed.

Figure 14:
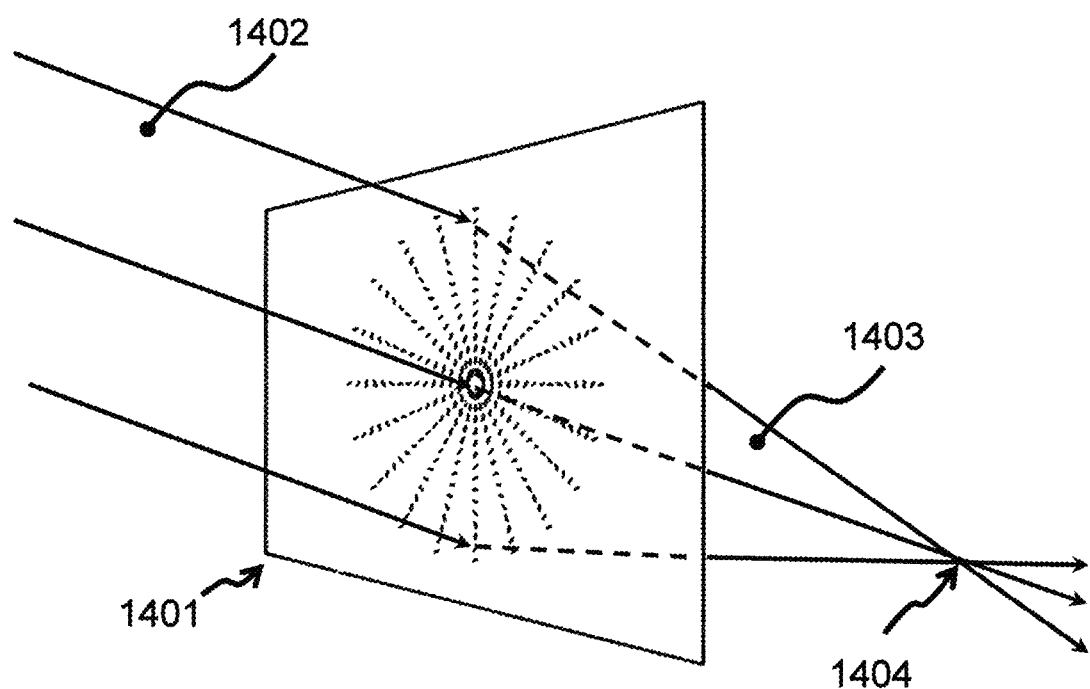
FIG. 14 is a schematic representation of a lens system employing at least one diffractive waveplate lens having a TUT CDW or TUT PVG structure, and diffracting an input beam that is incident at a steep angle of incidence.

Although the subject disclosure relates primarily to beam steering systems and field of view steering systems with large steering angles, it is obvious that the capability of an optic to handle large angles of incidence is desirable in many other systems besides beam steering systems. Such additional systems include diffractive waveplate lens systems with small f-number, and diffractive waveplate lens systems for which the angle of incidence of an input optical beam can be large. Based on the results disclosed herein, a lens system with small f-number, therefore with steep angles of incidence on at least some of the lenses of the lens system, and any lens system that may handle optical rays with steep angles of incidence, would have higher diffraction efficiency if it were fabricated with TUT or TUT PVG diffractive waveplate lenses than if it were fabricated with regular diffractive waveplate lenses. Such a diffractive waveplate lens system is illustrated in FIG. 14. For the case illustrated in FIG. 14, the diffractive waveplate lens system consists of a single diffractive waveplate lens 1401, shown with an input beam 1402 incident on the plane of the diffractive waveplate lens 1401 at a steep angle.

The terms "approximately"/"approximate"/"about" can be +/−10% of the amount referenced. Additionally, preferred amounts and ranges can include the amounts and ranges referenced without the prefix of being approximately/approximate/about.

Unless otherwise specifically noted, articles depicted in the drawings are not necessarily drawn to scale.

Although specific advantages have been enumerated above, various embodiments may include some, none, or all of the enumerated advantages.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

To aid the Patent Office and any readers of any patent issued on this application in interpreting the claims appended hereto, applicants wish to note that they do not intend any of the appended cairns or claim elements to invoke 35 U.S.C. 112(f) unless the words "means for" or "step for" are explicitly used in the particular claim.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A beam steering system comprising:
an optical assembly that includes at least one cycloidal diffractive waveplate, each cycloidal diffractive waveplate having three functional layers, in all of which an optical anisotropy axis is parallel to a surface of the cycloidal diffractive waveplate;
in outer two layers of at least one cycloidal diffractive waveplate, the optical anisotropy axis has an orientation varying linearly with position in a direction perpendicular to the surface of the cycloidal diffractive waveplate;
in an inner layer of at least one cycloidal diffractive waveplate, the optical anisotropy axis orientation having no variation with position in the direction perpendicular to the surface of the cycloidal diffractive waveplate;
a twist angle of the optical anisotropy axis orientation in one of the two outer layers of at least one cycloidal diffractive waveplate being equal in magnitude and opposite in sign to the twist angle of the optical anisotropy axis orientation of the other outer layer of the cycloidal diffractive waveplate; and
a product of thickness and birefringence of the outer two layers of at least one of the cycloidal diffractive waveplates being about 30% of an intended operating wavelength of the beam steering system;
a product of the thickness and birefringence of the inner layer of the at least one cycloidal diffractive waveplate being about 63% of the intended operating wavelength of the beam steering system;
an absolute value of the angle through which the optical anisotropy axis twists in the two outer layers of at least one cycloidal diffractive waveplate being about 82 degrees; and
a controller assembly configured and arranged such that propagation direction of a beam of optical radiation traversing the optical assembly is changed by a selected angle.

2. The beam steering system of claim 1, wherein the optical assembly comprises
a first cycloidal diffractive waveplate and a second cycloidal diffractive waveplate, the first cycloidal diffractive waveplate receiving a normally incident optical beam having a polarization volume grating structure providing high diffraction efficiency at a selected operating wavelength of the beam steering system;
the optical assembly includes components so that the rotational positions of the first and the second cycloidal diffractive waveplates are independently controlled by the controller assembly.

3. A beam steering system comprising:
an optical assembly that includes at least one cycloidal diffractive waveplate, each cycloidal diffractive waveplate having three functional layers, in all of which an optical anisotropy axis is parallel to a surface of the cycloidal diffractive waveplate;
in outer two layers of at least one cycloidal diffractive waveplate, the optical anisotropy axis has an orientation varying linearly with position in a direction perpendicular to the surface of the cycloidal diffractive waveplate;
in an inner layer of at least one cycloidal diffractive waveplate, the optical anisotropy axis orientation having no variation with position in the direction perpendicular to the surface of the cycloidal diffractive waveplate;
a twist angle of the optical anisotropy axis orientation in one of the two outer layers of at least one cycloidal diffractive waveplate being equal in magnitude and opposite in sign to the twist angle of the optical anisotropy axis orientation of the other outer layer of the cycloidal diffractive waveplate; and
a controller assembly configured and arranged such that propagation direction of a beam of optical radiation traversing the optical assembly is changed by a selected angle, wherein the optical assembly comprises:
a first set of N non-switchable cycloidal diffractive waveplates, all of which include lines of constant optical anisotropy axis orientation, the lines being parallel to each other both over an entire area of each non-switchable cycloidal diffractive waveplate, and among all members of the first set of N non-switchable cycloidal diffractive waveplates;
each member of the first set of N non-switchable cycloidal diffractive waveplates being preceded along a path of optical radiation propagating through the beam steering system by a switchable polarization converter that in one state converts left-hand circularly-polarized optical radiation to right-hand circularly-polarized optical radiation, and right-hand circularly-polarized optical radiation to left-hand circularly polarized optical radiation, and in the other state passes optical radiation without changing its polarization;
the number N being a positive integer equal to or greater than one.

4. The beam steering system of claim 1, wherein the optical assembly comprises:
a first set of N non-switchable cycloidal diffractive waveplates, all of which include lines of constant optical anisotropy axis orientation, the lines being parallel to each other both over an entire area of each non-switchable cycloidal diffractive waveplate, and among all members of the first set of N non-switchable cycloidal diffractive waveplates;
each member of the first set of N non-switchable cycloidal diffractive waveplates being preceded along a path of optical radiation propagating through the beam steering system by a switchable polarization converter that in one state converts left-hand circularly-polarized optical radiation to right-hand circularly-polarized optical radiation, and right-hand circularly-polarized optical radiation to left-hand circularly polarized optical radiation, and in the other state passes optical radiation without changing its polarization; and the number N being a positive integer equal to or greater than one.

5. The beam steering system of claim 3, further comprising:
 a second set of N non-switchable cycloidal diffractive waveplates, all of which include lines of constant optical anisotropy axis orientation, the lines being parallel to each other both over an entire area of each non-switchable cycloidal diffractive waveplate of the second set of N non-switchable cycloidal diffractive waveplates, and between each member of the second set of N non-switchable cycloidal diffractive waveplates, the lines of constant optical anisotropy axis orientation in the second set of non-switchable cycloidal diffractive waveplates being orthogonal to the lines of constant optical anisotropy axis orientation in the first set of non-switchable cycloidal diffractive waveplates;
 each member of the second set of N non-switchable cycloidal diffractive waveplates being preceded along a path of optical radiation propagating through the optical assembly of the beam steering system by a switchable polarization converter that in one state converts left-hand circularly-polarized optical radiation to right-hand circularly-polarized optical radiation, and right-hand circularly-polarized optical radiation to left-hand circularly polarized optical radiation, and in the other state passes optical radiation without changing its polarization.

6. The beam steering system of claim 4, further comprising:
 a second set of N non-switchable cycloidal diffractive waveplates, all of which include lines of constant optical anisotropy axis orientation, the lines being parallel to each other both over an entire area of each non-switchable cycloidal diffractive waveplate of the second set of N non-switchable cycloidal diffractive waveplates, and between each member of the second set of N non-switchable cycloidal diffractive waveplates, the lines of constant optical anisotropy axis orientation in the second set of non-switchable cycloidal diffractive waveplates being orthogonal to the lines of constant optical anisotropy axis orientation in the first set of non-switchable cycloidal diffractive waveplates;
 each member of the second set of N non-switchable cycloidal diffractive waveplates being preceded along a path of optical radiation propagating through the optical assembly of the beam steering system by a switchable polarization converter that in one state converts left-hand circularly-polarized optical radiation to right-hand circularly-polarized optical radiation, and right-hand circularly-polarized optical radiation to left-hand circularly polarized optical radiation, and in the other state passes optical radiation without changing its polarization.

7. An optical lens system comprising:
 at least one diffractive waveplate lens having three functional layers, in all of which an optical anisotropy axis is parallel to a surface of the at least one diffractive waveplate lens
 in outer two layers of the at least one of the diffractive waveplate lenses, the optical anisotropy axis orientation varying linearly with position in a direction perpendicular to a surface of the diffractive waveplate lens;
 in an inner layer of the at least one diffractive waveplate lens, the optical anisotropy axis orientation having no variation with position in a direction perpendicular to a surface of the at least one diffractive waveplate lens;
 a twist angle of the optical anisotropy axis orientation in one of the two outer layers of the at least one of the diffractive waveplate lenses being equal in magnitude and opposite in sign to a twist angle of the optical anisotropy axis orientation of the other outer layer of the at least one diffractive waveplate lens;
 a product of thickness and birefringence of the outer two layers of the at least one diffractive waveplate lens being about 30% of a selected operating wavelength of the optical lens system;
 a product of thickness and birefringence of the inner layer of the at least one diffractive waveplate lens being about 63% of the selected operating wavelength of the optical lens system; and
 an absolute value of an angle through which the optical anisotropy axis twists in the two outer layers of the at least one diffractive waveplate lens being about 82 degrees.

8. The beam steering system of claim 1, with an adjustment of the angles through which the orientation of the optical anisotropy axis varies within the three layers of the at least one cycloidal diffractive waveplate, the adjustment of the angles being such that the diffraction efficiency is approximately the same for a positive angle of incidence as for a negative angle of incidence.

* * * * *